United States Patent
Barzelay et al.

(10) Patent No.: US 12,390,492 B2
(45) Date of Patent: Aug. 19, 2025

(54) COMPOSITIONS AND METHODS FOR TREATING AGE-RELATED MACULAR DEGENERATION

(71) Applicants: Aya Barzelay, Ramat Gan (IL); Adiel Barak, Hod Hasharon (IL); Anat Loewenstein, Tel Aviv (IL)

(72) Inventors: Aya Barzelay, Ramat Gan (IL); Adiel Barak, Hod Hasharon (IL); Anat Loewenstein, Tel Aviv (IL)

( * ) Notice: Subject to any disclaimer, the term of this patent is extended or adjusted under 35 U.S.C. 154(b) by 1382 days.

(21) Appl. No.: 16/978,735

(22) PCT Filed: Mar. 7, 2019

(86) PCT No.: PCT/IL2019/050258
§ 371 (c)(1),
(2) Date: Sep. 7, 2020

(87) PCT Pub. No.: WO2019/171386
PCT Pub. Date: Sep. 12, 2019

(65) Prior Publication Data
US 2020/0397825 A1  Dec. 24, 2020

Related U.S. Application Data

(60) Provisional application No. 62/639,648, filed on Mar. 7, 2018.

(51) Int. Cl.
*A61K 35/28* (2015.01)
*A61P 27/02* (2006.01)
*C12N 5/077* (2010.01)
*C12N 5/0775* (2010.01)

(52) U.S. Cl.
CPC .............. *A61K 35/28* (2013.01); *A61P 27/02* (2018.01); *C12N 5/0654* (2013.01); *C12N 5/0667* (2013.01); *C12N 2500/02* (2013.01); *C12N 2502/1382* (2013.01)

(58) Field of Classification Search
CPC ......... A61K 35/28; A61K 38/19; A61P 27/02; A61P 25/02; C12N 5/0654; C12N 5/0667; C12N 2500/02; C12N 2502/1382; C12N 5/0621
See application file for complete search history.

(56) References Cited

FOREIGN PATENT DOCUMENTS

WO   2013082543 A1   6/2013

OTHER PUBLICATIONS

Nepali (Nepali, Sarmila et al. "Comparative Analysis of Human Adipose-Derived Mesenchymal Stem Cells from Orbital and Abdominal Fat." Stem cells international vol. 2018 3932615. Aug. 19, 2018) (Year: 2018).*

Wester, S.T. Orbital Stem Cells. Curr Ophthalmol Rep 2, 107-115 (2014). (Year: 2014).*

(Continued)

*Primary Examiner* — Tracy Vivlemore
*Assistant Examiner* — Thomas R. Amick
(74) *Attorney, Agent, or Firm* — The Roy Gross Law Firm, LLC; Roy Gross

(57) ABSTRACT

The present invention is directed to compositions for treating oxidative-stress related-damage of retinal pigment epithelium (RPE) cells by contacting orbital fat-derived mesenchymal cell with the damaged RPE cells.

17 Claims, 21 Drawing Sheets
Specification includes a Sequence Listing.

(56) References Cited

OTHER PUBLICATIONS

A. Barzelay, R. Levy, E. Kohn, M. Sella, N. Shani, B. Meilik, E. Gur, A. Loewenstein, A. Barak, Laboratory of Ophthalmology Department of Ophthalmology Tel Aviv Medical Center; Therapeutic potential of adipose tissue derived mesenchymal stem cells for AMD—migration, trophic anti-angiogenic effects and differentiation. Invest. Ophthalmol. Vis. Sci. 2015;56(7):1826.
Li Y, Reca RG, Atmaca-Sonmez P, Ratajczak MZ, Ildstad ST, Kaplan HJ, Enzmann V. Retinal pigment epithelium damage enhances expression of chemoattractants and migration of bone marrow-derived stem cells. Invest Ophthalmol Vis Sci. Apr. 2006;47(4):1646-52. doi: 10.1167/iovs.05-1092. PMID: 16565405.
Oner, A., Gonen, Z. B., Sinim, N., Cetin, M., & Ozkul, Y. (2016). Subretinal adipose tissue-derived mesenchymal stem cell implantation in advanced stage retinitis pigmentosa: a phase I clinical safety study. Stem cell research & therapy, 7 (1), 178. https://doi.org/10.1186/s13287-016-0432-y.
Tsuji, W., Rubin, J. P., & Marra, K. G. (2014). Adipose-derived stem cells: Implications in tissue regeneration. World journal of stem cells, 6(3), 312-321. https://doi.org/10.4252/wjsc.v6.i3.312.
Ferraro GA, De Francesco F, Nicoletti G, Paino F, Desiderio V, Tirino V, D'Andrea F. Human adipose CD34+ CD90+ stem cells and collagen scaffold constructs grafted in vivo fabricate loose connective and adipose tissues. J Cell Biochem. May 2013;114(5):1039-49. doi: 10.1002/jcb.24443. PMID: 23129214.
Zuk PA, Zhu M, Mizuno H, Huang J, Futrell JW, Katz AJ, Benhaim P, Lorenz HP, Hedrick MH. Multilineage cells from human adipose tissue: implications for cell-based therapies. Tissue Eng. Apr. 2001;7(2):211-28. doi: 10.1089/107632701300062859. PMID: 11304456.
Kannan, R., & Hinton, D. R. (2014). Sodium iodate induced retinal degeneration: new insights from an old model. Neural regeneration research, 9(23), 2044-2045. https://doi.org/10.4103/1673-5374.147927.
Rochefort GY, Delorme B, Lopez A, Hérault O, Bonnet P, Charbord P, Eder V, Domenech J. Multipotential mesenchymal stem cells are mobilized into peripheral blood by hypoxia. Stem Cells. Oct. 2006;24(10):2202-8. doi: 10.1634/stemcells.2006-0164. Epub Jun. 15, 2006. PMID: 16778152.
Li S, Deng Y, Feng J, Ye W. Oxidative preconditioning promotes bone marrow mesenchymal stem cells migration and prevents apoptosis. Cell Biol Int. Mar. 2009;33(3):411-8. doi: 10.1016/j.cellbi.2009.01.012. Epub Jan. 24, 2009. PMID: 19356708.
Valle-Prieto A, Conget PA. Human mesenchymal stem cells efficiently manage oxidative stress. Stem Cells Dev. Dec. 2010;19(12):1885-93. doi: 10.1089/scd.2010.0093. Epub Aug. 18, 2010. PMID: 20380515.
Bhutto IA, McLeod DS, Merges C, Hasegawa T, Lutty GA. Localisation of SDF-1 and its receptor CXCR4 in retina and choroid of aged human eyes and in eyes with age related macular degeneration. Br J Ophthalmol. Jul. 2006;90(7):906-10. doi: 10.1136/bjo.2006.090357. Epub Apr. 5, 2006. PMID: 16597663; PMCID: PMC1857162.

Singh T, Prabhakar S, Gupta A, Anand A. Recruitment of stem cells into the injured retina after laser injury. Stem Cells Dev. Feb. 10, 2012;21(3):448-54. doi: 10.1089/scd.2011.0002. Epub Jul. 28, 2011. PMID: 21561324.
Hanus J, Anderson C, Wang S. RPE necroptosis in response to oxidative stress and in AMD. Ageing Res Rev. Nov. 2015;24(Pt B):286-98. doi: 10.1016/j.arr.2015.09.002. Epub Sep. 11, 2015. PMID: 26369358; PMCID: PMC4661094.
Barzelay A, Levy R, Kohn E, Sella M, Shani N, Meilik B, Entin-Meer M, Gur E, Loewenstein A, Barak A. Power-Assisted Liposuction Versus Tissue Resection for the Isolation of Adipose Tissue-Derived Mesenchymal Stem Cells: Phenotype, Senescence, and Multipotency at Advanced Passages. Aesthet Surg J. Sep. 2015;35(7):NP230-40. doi: 10.1093/asj/sjv055. PMID: 26319084.
Shevach M, Zax R, Abrahamov A, Fleischer S, Shapira A, Dvir T. Omentum ECM-based hydrogel as a platform for cardiac cell delivery. Biomed Mater. May 13, 2015;10(3):034106. doi: 10.1088/1748-6041/10/3/034106. PMID: 25970726.
Tezel TH, Del Priore LV, Berger AS, Kaplan HJ. Adult retinal pigment epithelial transplantation in exudative age-related macular degeneration. Am J Ophthalmol. Apr. 2007;143(4):584-95. doi: 10.1016/j.ajo.2006.12.007. Epub Feb. 14, 2007. PMID: 17303061.
Otani A, Kinder K, Ewalt K, Otero FJ, Schimmel P, Friedlander M. Bone marrow-derived stem cells target retinal astrocytes and can promote or inhibit retinal angiogenesis. Nat Med. Sep. 2002;8(9):1004-10. doi: 10.1038/nm744. Epub Jul. 29, 2002. PMID: 12145646.
Arnhold S, Heiduschka P, Klein H, et al. Adenovirally transduced bone marrow stromal cells differentiate into pigment epithelial cells and induce rescue effects in RCS rats. Investigative Ophthalmology & Visual Science. Sep. 2006;47(9):4121-4129. DOI: 10.1167/iovs.04-1501. PMID: 16936132.
Vossmerbaeumer U, Ohnesorge S, Kuehl S, Haapalahti M, Kluter H, Jonas JB, Thierse HJ, Bieback K. Retinal pigment epithelial phenotype induced in human adipose tissue-derived mesenchymal stromal cells. Cytotherapy. 2009;11(2):177-88. doi: 10.1080/14653240802714819. PMID: 19241195.
Gong L, Wu Q, Song B, Lu B, Zhang Y. Differentiation of rat mesenchymal stem cells transplanted into the subretinal space of sodium iodate-injected rats. Clin Exp Ophthalmol. Oct. 2008;36(7):666-71. doi: 10.1111/i.1442-9071.2008.01857.x. PMID: 18983552.
Ho JH, Ma WH, Tseng TC, Chen YF, Chen MH, Lee OK. Isolation and characterization of multi-potent stem cells from human orbital fat tissues. Tissue Eng Part A. Jan. 2011;17(1-2):255-66. doi: 10.1089/ten.TEA.2010.0106. Epub Nov. 29, 2010. PMID: 20726817.
Chen SY, Mahabole M, Horesh E, Wester S, Goldberg JL, Tseng SC. Isolation and characterization of mesenchymal progenitor cells from human orbital adipose tissue. Invest Ophthalmol Vis Sci. Jul. 3, 2014;55(8):4842-52. doi: 10.1167/iovs.14-14441. PMID: 24994870; PMCID: PMC4123896.
PCT International Search Report for International Application No. PCT/IL2019/050258, mailed Aug. 8, 2019, 6pp.
PCT Written Opinion for International Application No. PCT/IL2019/050258, mailed Aug. 8, 2019, 7pp.

* cited by examiner

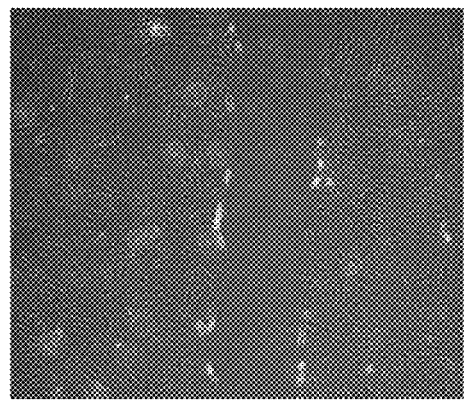
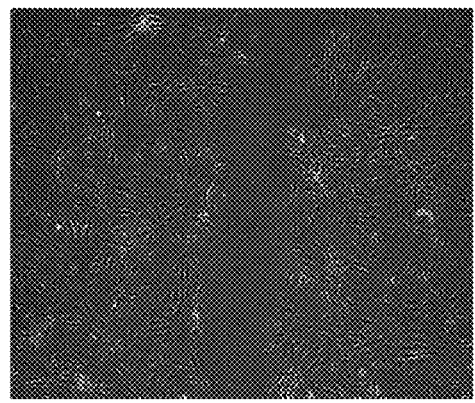
FIGURE 2E                    FIGURE 2F
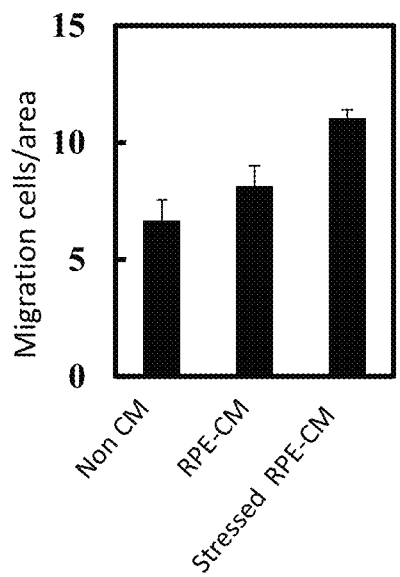
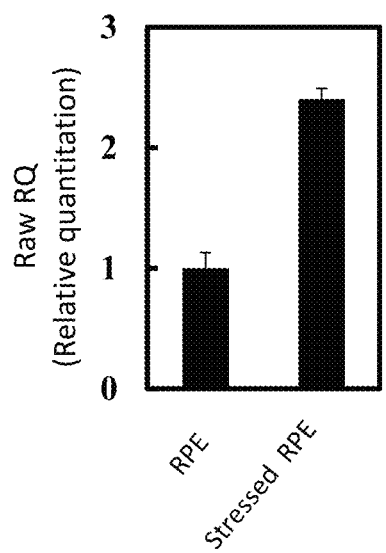
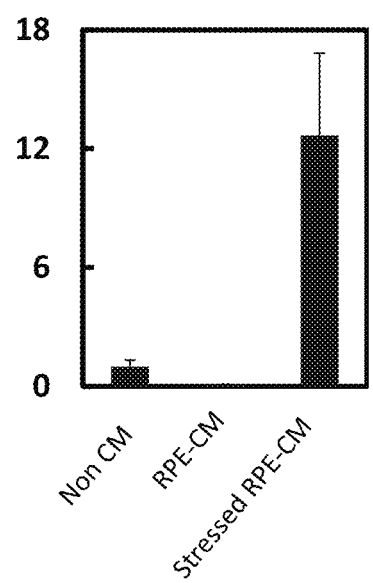
FIGURE 2G        FIGURE 2H        FIGURE 2I

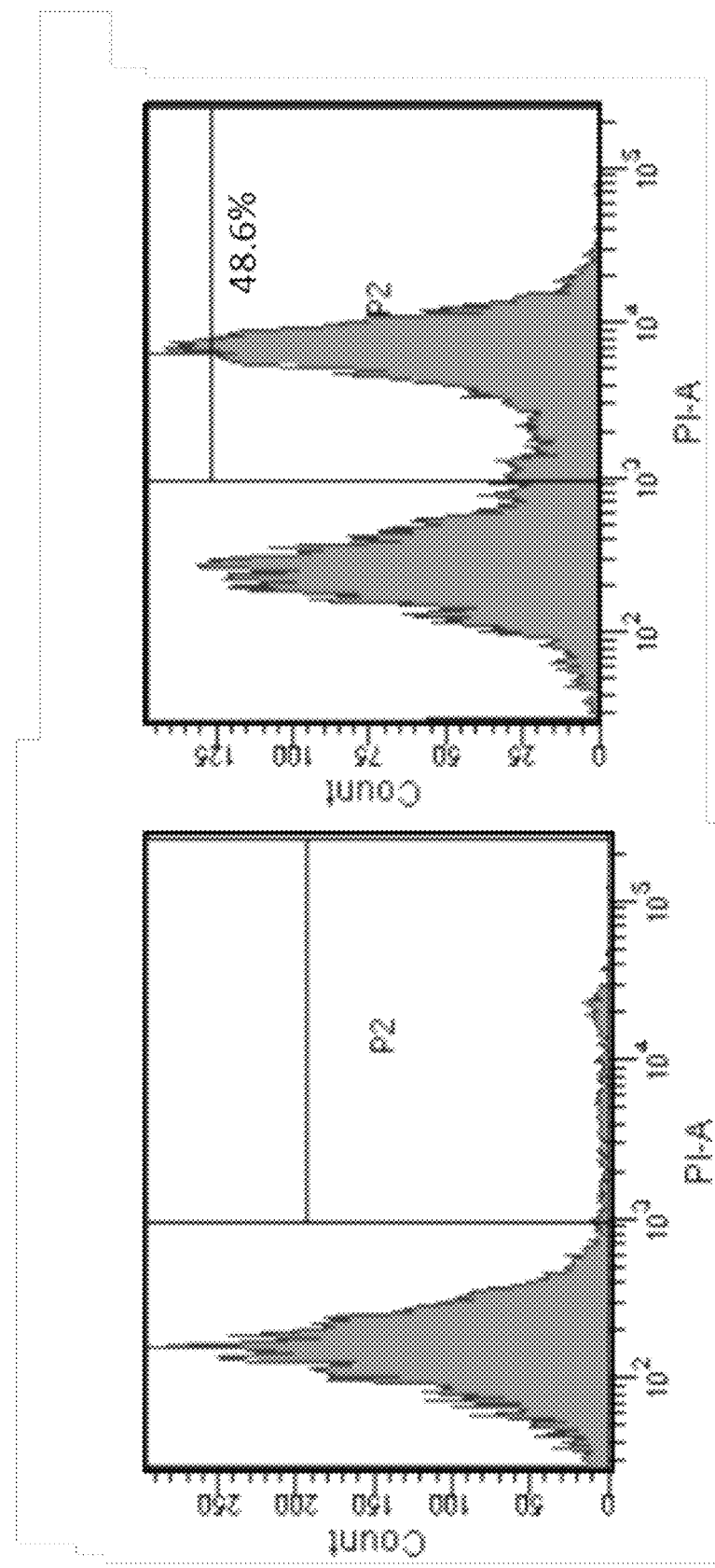

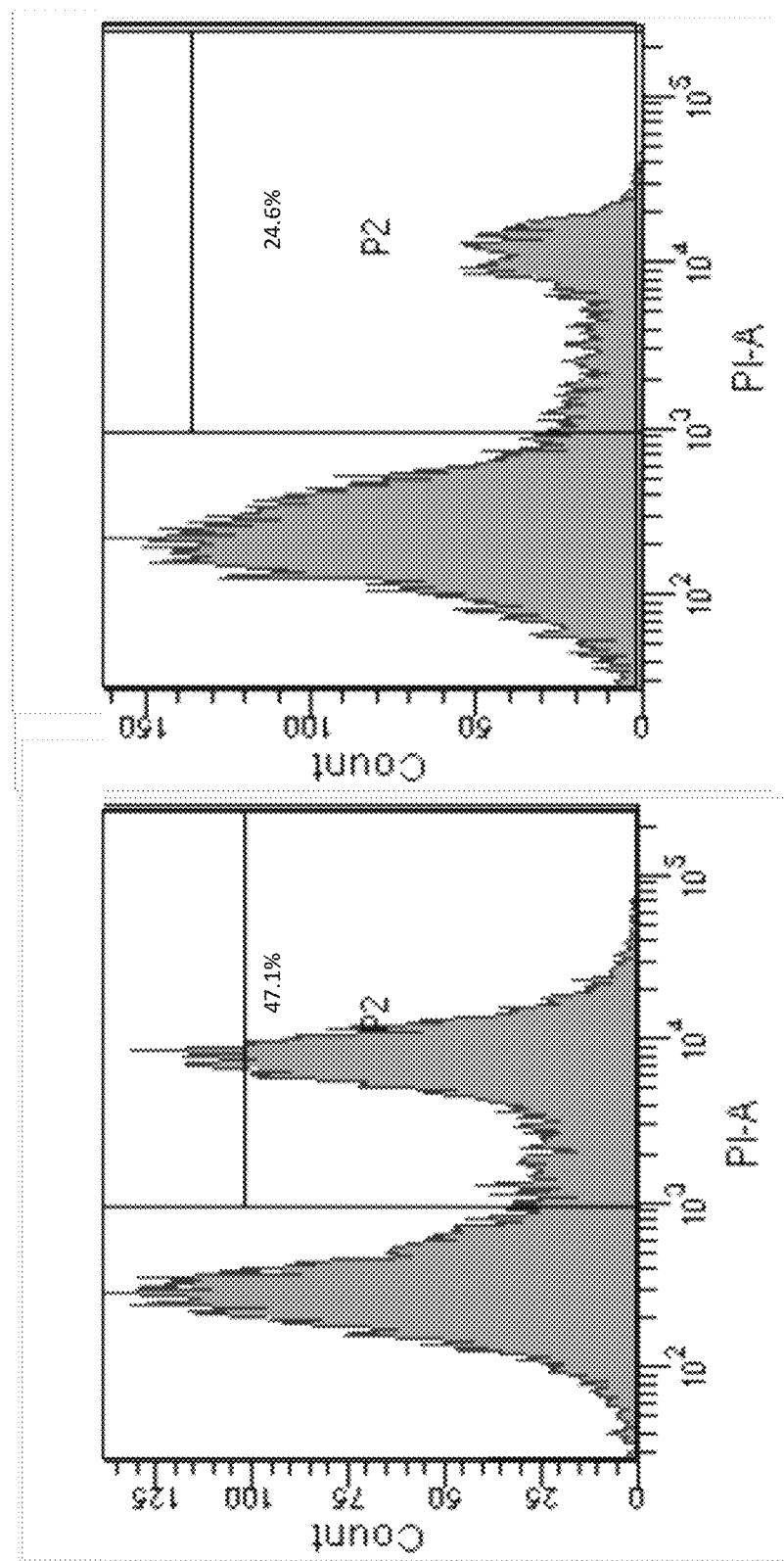

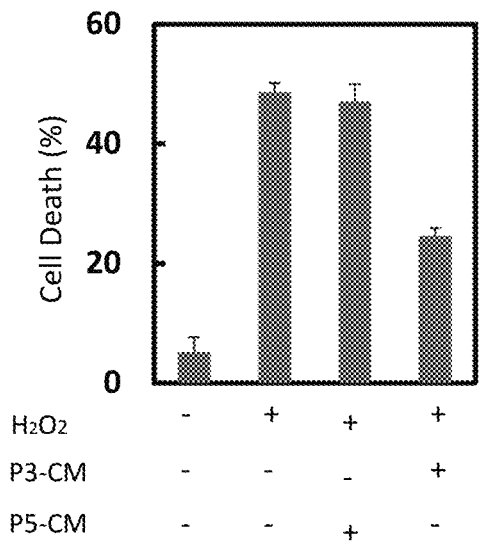
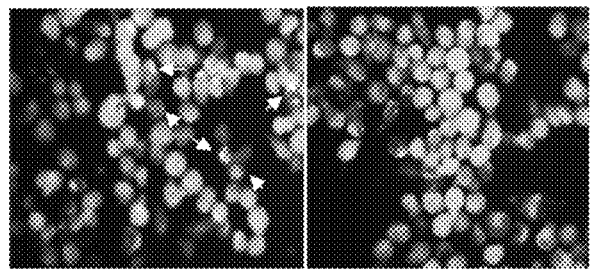
FIGURE 3F  FIGURE 3G
FIGURE 3E
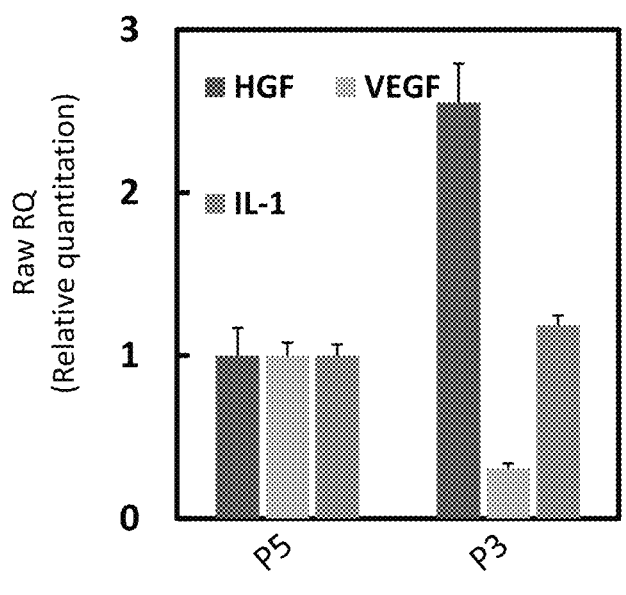
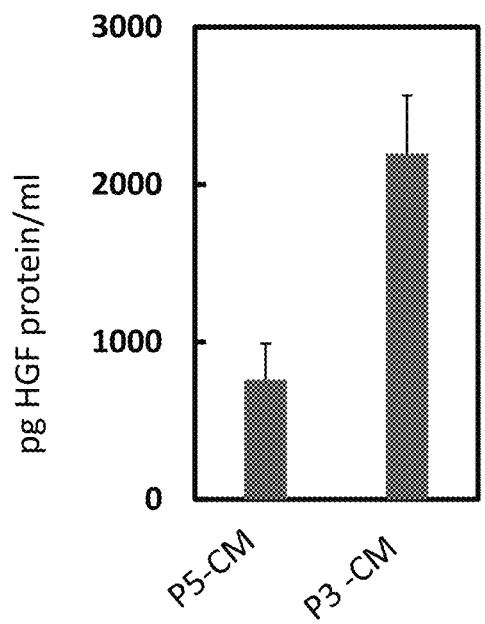
FIGURE 4A  FIGURE 4B

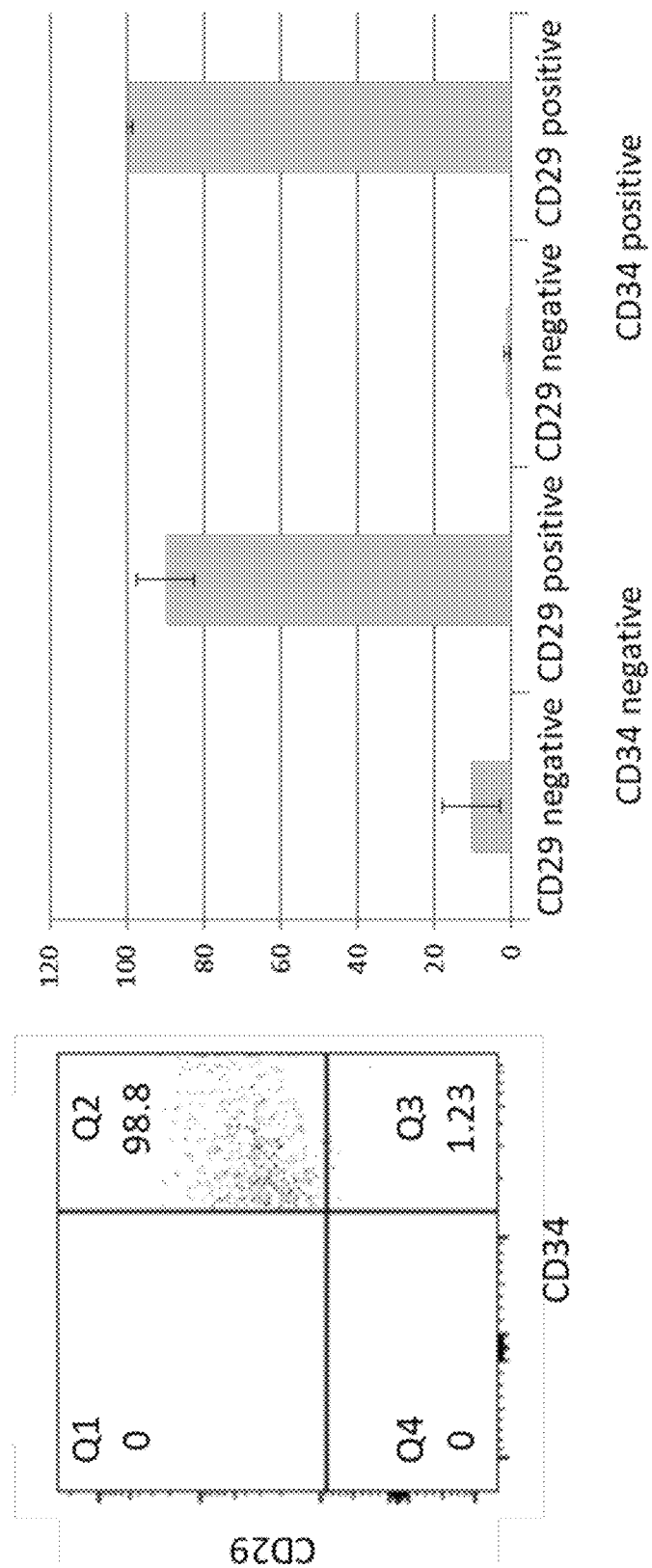

COMPOSITIONS AND METHODS FOR TREATING AGE-RELATED MACULAR DEGENERATION

CROSS REFERENCE TO RELATED APPLICATIONS

This application is a National Phase of PCT Patent Application No. PCT/IL2019/050258 having International filing date of Mar. 7, 2019, which claims the benefit of priority under 35 U.S.C. § 119 (e) of U.S. Provisional Patent Application No. 62/639,648, filed Mar. 7, 2018. The contents of the above applications are all incorporated by reference as if fully set forth herein in their entirety.

FIELD OF INVENTION

The present invention is in the field of regenerative medicine.

BACKGROUND OF THE INVENTION

Dysfunction of the retinal pigment epithelium (RPE) has been linked to various eye disorders such as age-related macular degeneration (AMD), as well as hereditary disorders such as retinitis pigmentosa (RP). AMD is the leading cause of blindness in patients over 60 years old in western countries. Although the pathophysiology of AMD is not fully understood, it is known that degeneration of RPE has a cardinal role in disease progression. Ninety percent (90%) of AMD patients suffer from non-neovascular AMD, which is characterized by both neural retinal atrophy and choroidal vascular atrophy. Lifestyle modification and vitamin supplements are currently the only treatment option for non-neovascular AMD; however, this can only stop the progression of the disease and is unable to reverse damage to the macula. Ten percent of non-neovascular AMD patients will progress to neovascular AMD, which is characterized by choroidal neovascularization. It is a progressive condition that can lead to a severe and rapid loss of vision. To date, Anti-vascular endothelial growth factor (VEGF) antibodies have been used to treat neovascular AMD. However, this treatment is also not curative, and is only aimed at prevention of further vision deterioration.

Cell therapy aiming to replace the non-functional RPE may lead to favorable results. To date, transplantations of various cell types have achieved limited results.

MSCs (mesenchymal stem cells) are adult multipotent stem cells, which can be isolated from an adipose tissue and are capable of self-renewal, differentiate to several cell lineages, and have a paracrine trophic effect. In addition, MSCs were shown to be hypoimmunogenic, making them suitable for allogeneic transplantations.

Unlike most adipose tissue, which is derived from mesoderm, the orbital connective tissue is of neural crest origin, like most ocular and orbital tissues. On this note, adipose stem cells (ASCs) are known to be unable to differentiate into corneal epithelial cells. Based on the latter, orbital fat derived-MSCs are suggested to be more potent with respect to differentiation capacity to RPE, due to their proximity to the eye, mutual embryonic origin, and proven differentiation potential to other ophthalmic tissue.

SUMMARY OF THE INVENTION

The present invention relates to compositions and methods for treating oxidative-stress related-damage of retinal pigment epithelium (RPE) cells. In some embodiments, a use or administration of a composition comprising orbital fat-derived mesenchymal cells for treatment of age-related macular disease (AMD) in a subject, is provided. In some embodiments, the present invention is directed to a method for preparing a therapeutic composition enhancing oxidative stress-related-protecting activity of orbital fat-derived mesenchymal cells.

According to one aspect, there is provided a composition comprising mesenchymal cells and a carrier, wherein at least 70% of the cells within the composition express CD73, CD90 and CD105; and at least 70% of the cells lack expression of CD45.

In some embodiments, at least 70% of the mesenchymal cells further express CXCR4. In some embodiments, at least 30% of the mesenchymal cells express CD34. In some embodiments, mesenchymal cells are orbital fat derived mesenchymal cells. In some embodiments, at least 50% of the mesenchymal cells express an anti-inflammatory cytokine. In some embodiments, at least 50% of the mesenchymal cells express a neurotrophic cytokine. In some embodiments, at least 50% of the mesenchymal cells are migratory cells. In some embodiments, further provided is a scaffold carrying the mesenchymal cells.

According to another aspect, there is provided a method for preventing degeneration of RPE in a subject, comprising contacting oxidatively-stressed RPE cells with a composition comprising mesenchymal cells, wherein at least 70% of cells within the composition express CD73, CD90 and CD105; and at least 70% of the cells lack expression of CD45, thereby preventing degeneration of the RPE.

According to another aspect, there is provided a method for treating age-related macular degeneration (AMD) in a subject, comprising the step of contacting oxidatively-stressed RPE cells with a therapeutically effective amount of a composition comprising mesenchymal cells, wherein at least 70% of the cells within the composition express CD73, CD90 and CD105; and at least 70% of the cells lack expression of CD45, thereby treating AMD in the subject.

In some embodiments, the mesenchymal cells are autologous or allogeneic cells.

According to another aspect, there is provided a method for preparing a therapeutic AMD cell composition, the method comprising: providing oxidatively-stressed RPE cells or a culture medium derived from the stressed RPE cells; and contacting for at least 24 hours mesenchymal cells expressing CD34, CD73, CD90 and CD105; and lacking the expression of CD45, with the stressed RPE cells or the culture medium derived from the stressed RPE cells.

In some embodiments, further provided is a step of screening the cells for: over expression of CXCR4 by at least 2-fold, increased cell migration by at least 25%, or a combination thereof. In some embodiments, further provided is a step of screening the cells for: expression of any eyefield marker selected form the group consisting of: paired box protein-6 (PAX6), orthodenticle homeobox 2 (OTX2), SIX homeobox 3 (SIX3), or any combination thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 2A-2I are images and graphs demonstrate enhanced migration of Adipose derived mesenchymal stem cell (ASCs) following exposure to stressed RPE cells. The migratory ability of ASCs was compared before (2A) and after 24 hours exposure (2B) to stressed RPE-CM (RPE treated with $H_2O_2$), or to controls comprising ASCs before (2C) or after 24 hours exposure (2D) to RPE-CM (RPE cultured without $H_2O_2$) and non-CM (non-conditioned ADSC medium) at time 0 (2E) and after 24 hours (2F). Micrographs shown are at 10× magnification. (2G) is a vertical bar graph showing quantification of ASCs' migration by counting invasive cells in scratch boundaries. ASCs and RPE cells were harvested and mRNA levels were analyzed using qRT-PCR. (2H) is a vertical bar graph showing SDF-1 mRNA in RPE cells incubated with or without $H_2O_2$. (2I) is a vertical bar graph showing CXCR4 mRNA in ASCs incubated with stressed RPE-CM, RPE-CM or non-CM. CXCR4: chemokine receptor type 4, SDF1: stromal cell-derived factor 1, RPE: retinal pigment epithelium, ASCs: Adipose-Derived stem cells, CM: conditioned medium.

FIGS. 3A-3G are images and graphs demonstrating that ASCs rescue RPE from necrosis under oxidative stress. RPE cells were incubated with ASCs' conditioned medium at passage 3 (3D; P3-CM), or with controls comprising of ASCs' conditioned medium at passage 5 (3C; P5-CM) or non-conditioned ADSC medium (3B; non-CM) for 48 hours, followed by exposure to $H_2O_2$ (1 mM, 7 h). Intact RPE were also used as control (3A). Cells were harvested, cell-death was analyzed using PI staining followed by flow cytometer analysis, and results were summarized in vertical bar graph (3E). (3F-3G) are fluorescent images of cell death visualized in RPE cells which were incubated with ASCs' conditioned medium at passage 3 (3F) or non-conditioned ADSC medium (3G) by acridine orange and ethidium bromide staining. Dying cells incorporated both acridine orange and ethidium bromide and are co-stained (arrows; orange color). Live cells appear green stained by acridine orange only (20× magnification). CM: condition medium, PI: Propidium iodide.

FIGS. 4A-4B are vertical bar graphs describing ASCs overexpress the neurotropic protein HGF but not VEGF nor the pro-inflammatory cytokine Il-1β. ASCs at passage 3 that were cultured in serum free conditions for 48 hours were compared to control group of ASCs at passage 5. Both cells and medium were collected and analyzed at mRNA level and at protein level by qRT-PCR and by ELISA, respectively. (4A) is a bar graph of qRT-PCR analysis of HGF, VEGF and IL-1β. (4B) is a bar graph of ELISA analysis for HGF protein levels.

FIGS. 15A-15D are graphs showing identification of cell sub-populations using an antibody panel. (15A) is a graph showing the distribution of CD34 positive and negative orbital adipose stem cells (ORBASC). The distribution of CD29 positive cells among these cells was further examined. Representative result of population distribution of the CD29 expression within CD34 negative (15B) and positive (15C) cells. (15D) is a vertical bar graph summarizing the quantification results of 5 examined ORBASC samples.

DETAILED DESCRIPTION OF THE INVENTION

Figure 1A:
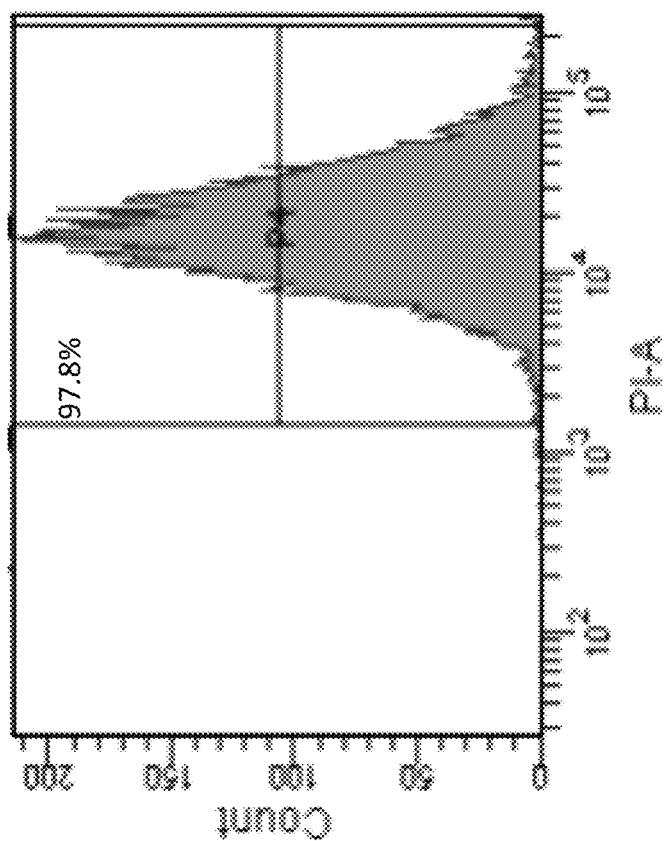
FIGS. 1A-1J are graphs and images showing characterization of Adipose derived mesenchymal stem cell (ASCs) by surface phenotype and differentiation potential at passage 3. (1A-1E) are graphs resulting from Fluorescence-activated cell sorting (FACS) analysis of cultured ASCs at passage 3 were detached with trypsin, equally dispensed into FACS tubes ($1\times10^5$ cells per tube), and incubated with monoclonal antibodies against human CD90 (1A), CD105 (1B), CD73 (1C), CD34 (1D), CD45 (1E), and CD29 (1F). Cells were then analyzed by flow cytometry for the expression of cell surface markers. (1G-1J) are micrographs showing multipotency of ASCs. Differentiation media was introduced to ASCs for 2 weeks. Differentiation to adipocytes was assessed using an Oil Red O stain on day 1 (1G) or day 14 (1I) post seeding. Bone differentiation was assessed using Alizarin red on day 1 (1H) or day 14 (1J) post seeding. (10× magnification). ASCs: Adipose-Derived stem cells, CD: cluster of differentiation.
Figure 1B:
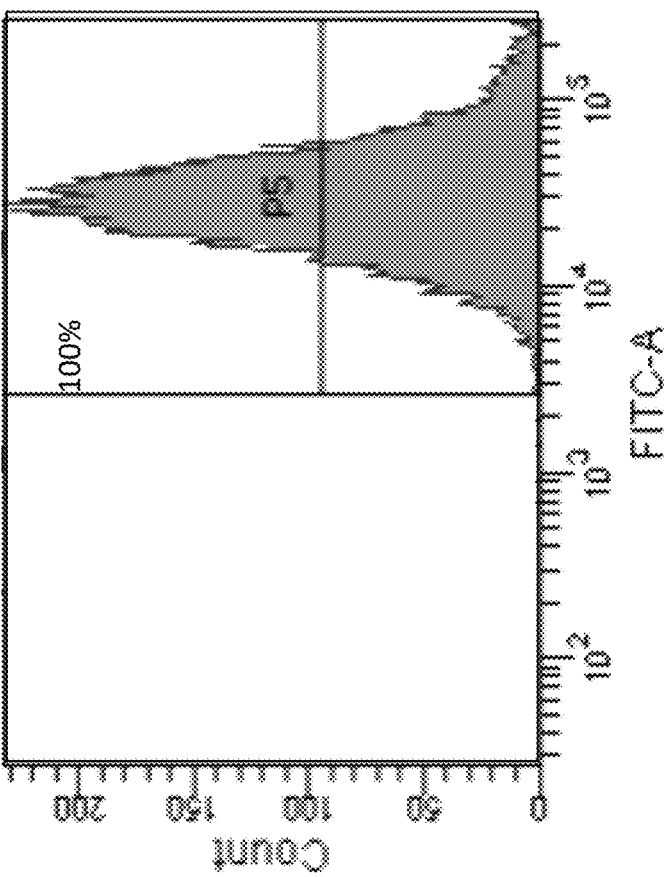
Figure 1C:
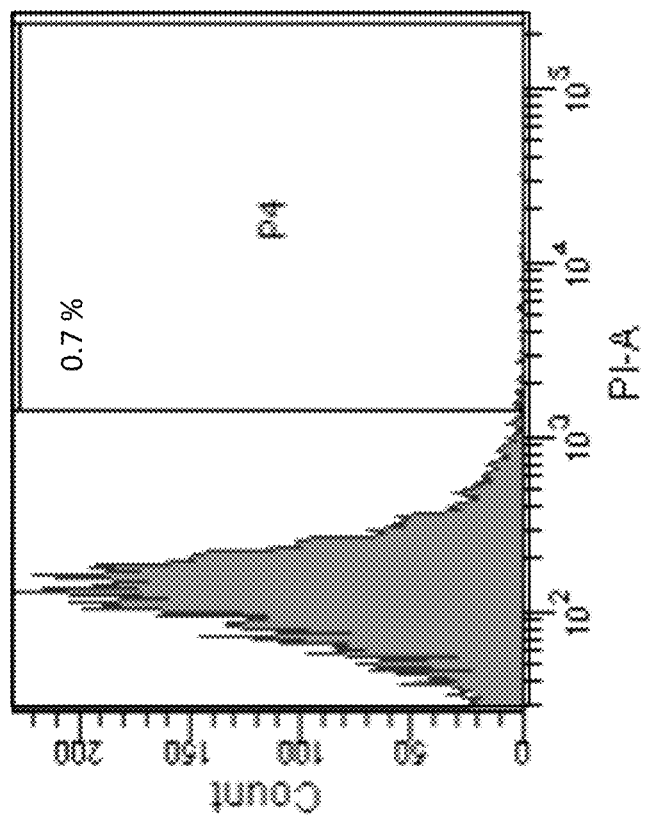
Figure 1D:
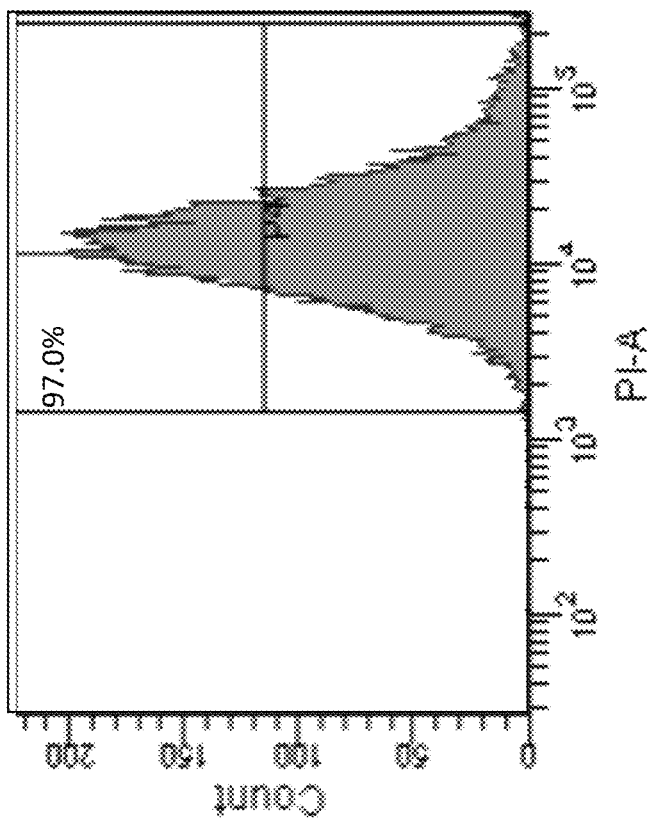
Figure 1E:
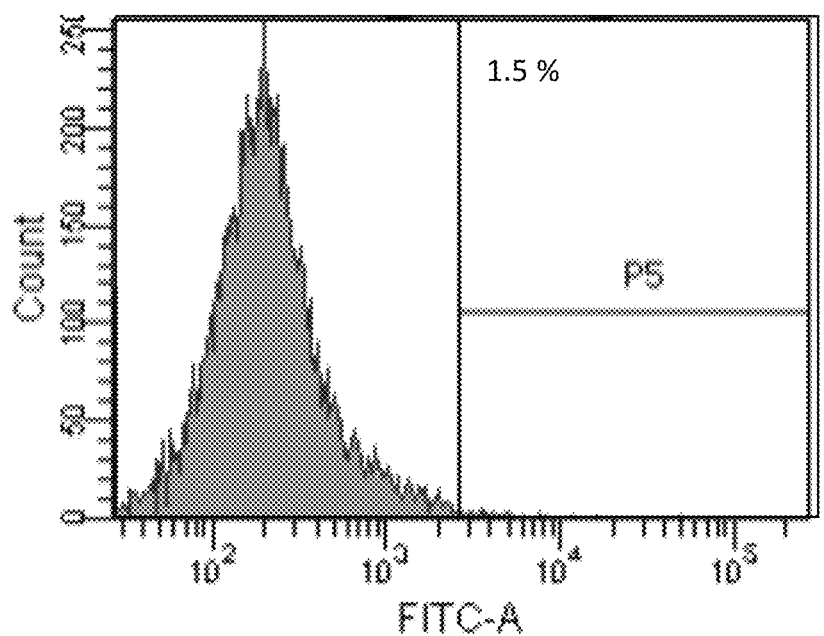
Figure 1F:
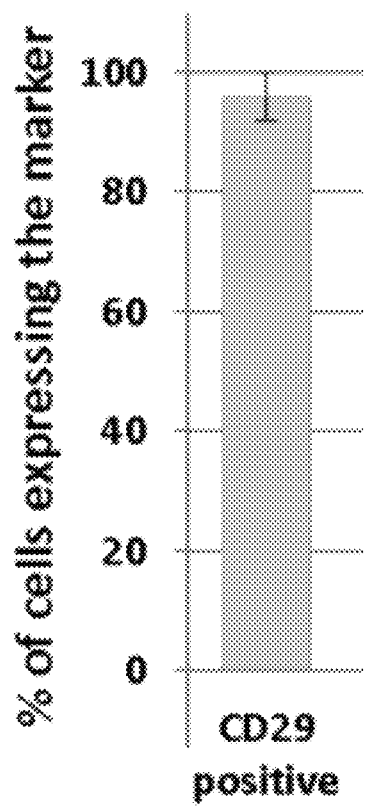
Figure 1G:
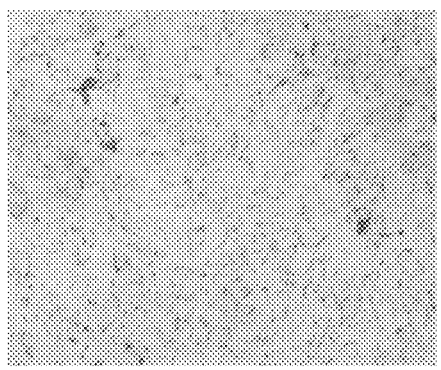
Figure 1H:
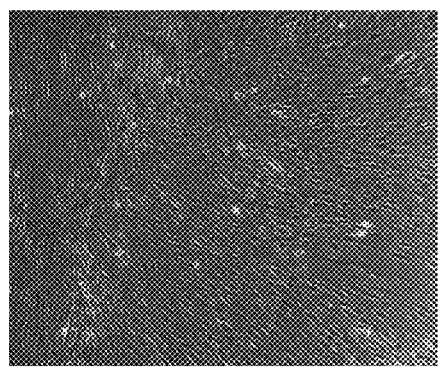
Figure 1I:
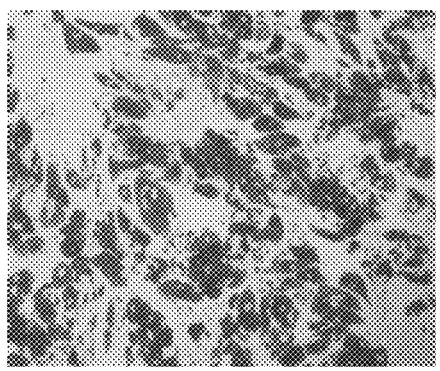
Figure 1J:
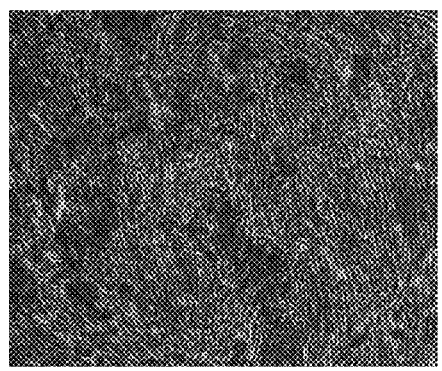
Figure 2A:
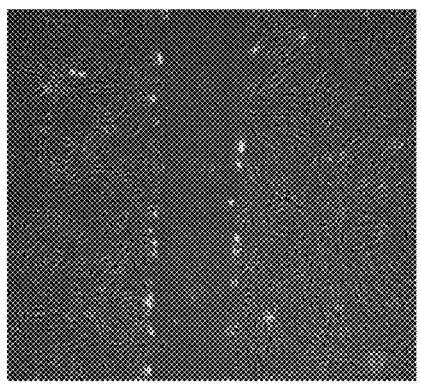
Figure 2B:
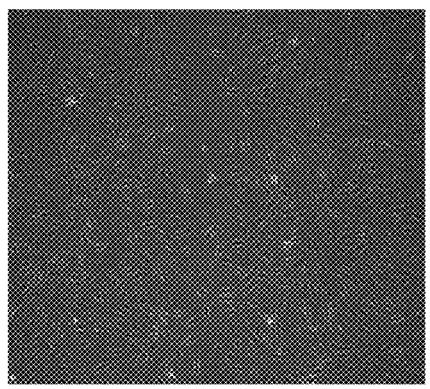
Figure 2C:
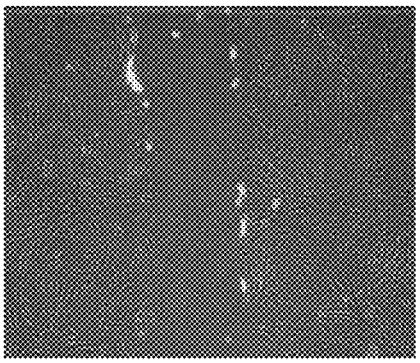
Figure 2D:
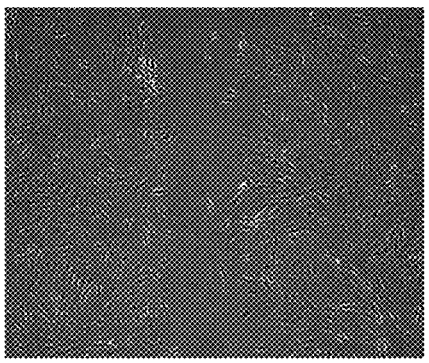
Figure 5A:
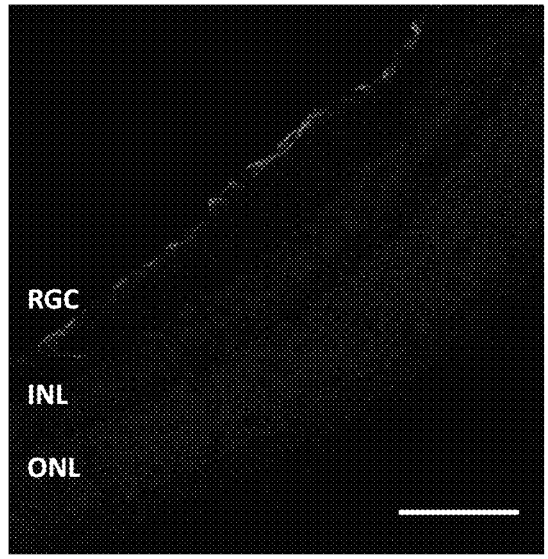
FIGS. 5A-5D are fluorescent images demonstrating Müller cell activation. Retinal slices were stained for the glial fibrillary acidic protein (GFAP antibody; pink) and cell nuclei (DAPI; blue). Müller cell activation was induced using $NaIO_3$. No $NaIO_3$ treatment (5A); $NaIO_3$ treatment only (5B); $NaIO_3$ treatment and Phosphate buffer saline (PBS) (5C); and $NaIO_3$ treatment and ASCs treatment (5D). Müller cell activation was seen in all the eyes that were exposed to $NaIO_3$ (arrow heads) but more so in eyes that received sub-retinal injection. No difference was observed between the control and experiment groups. Bar=100 μm, ONL—outer nuclear layer, INL—inner nuclear layer, RGC—retinal ganglion layer.
Figure 5B:
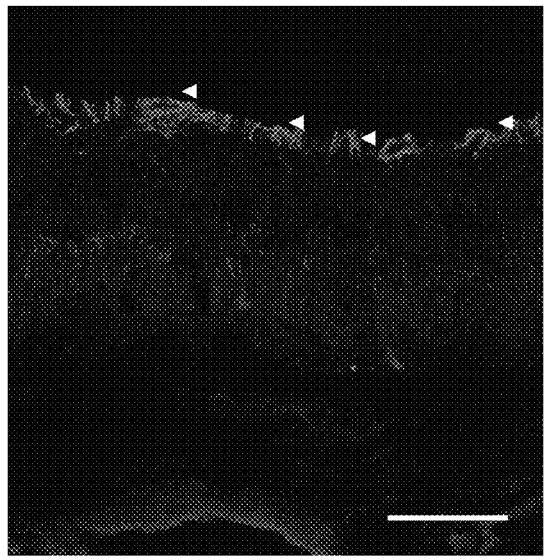
Figure 5C:
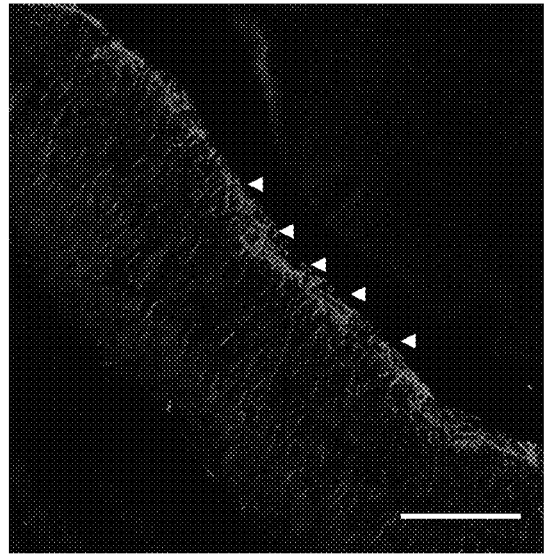
Figure 5D:
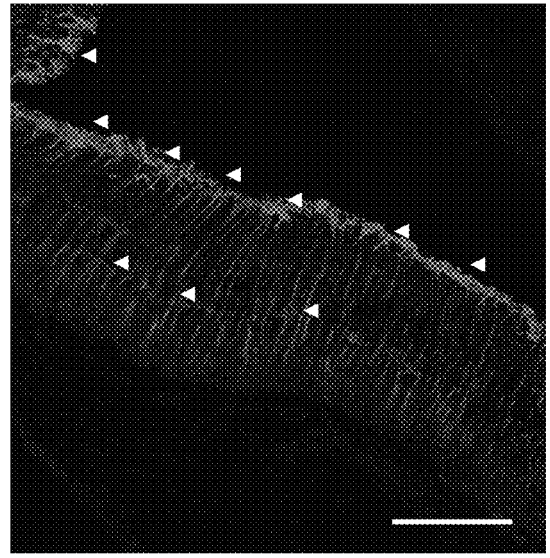

The present invention relates to compositions and methods for treating oxidative-stress related-damage of retinal pigment epithelium (RPE) cells. In some embodiments, there is provided use or administration of a composition comprising orbital fat-derived mesenchymal stem cells (OMSC) for treatment of age-related macular disease (AMD) in a subject. In some embodiments, the present invention provides a method for preparing a therapeutic composition enhancing oxidative stress-related-protecting activity of OMSCs. In one embodiment, oxidative-stress related-damage of retinal pigment epithelium (RPE) cells comprises AMD.

Cells

In some embodiments, cells of the present invention are mesenchymal cells. In some embodiments, mesenchymal cells comprise mesenchymal stem cells (MSCs). In some embodiments, mesenchymal cells comprise progenitor cells such as but not limited to progenitors of: osseous cell, adipose cell, cartilaginous cell, and/or connective tissue cell. In some embodiments, a MSC is an adipose-derived mesenchymal stem cell. In some embodiments, MSC is an orbital fat-derived mesenchymal stem cell (OMSC). In some embodiments, MSC includes progenitor cells. In some embodiments, mesenchymal cell or MSC or a mesenchymal progenitor cell is derived from orbital fat. In some embodiments, the term "cells" or "cell" includes a composition comprising MSC, mesenchymal cells, OMSC/s, mesenchymal progenitor cells, or any combination thereof. In some embodiments, the term "cells" or "cell" includes a composition comprising MSC, mesenchymal cells, OMSC/s, mesenchymal progenitor cells selected from, isolated from, obtained from, or derived from orbital fat.

In one embodiment, orbital fat comprises a redundant orbital fat tissue of the intraorbital cavity. In another embodiment, orbital fat tissue of the intraorbital cavity is dissected in a blepharoplastic surgeries. In one embodiment, collected orbital fat tissue is mechanically and enzymatically fragmented and/or disassociated. In one embodiment, fragmented tissue is filtered, washed, centrifuged, or any combination thereof. In one embodiment, centrifuged pellet comprises OMSCs.

As would be apparent to one of ordinary skill in the art, OMSCs can be verified by cell profiling based on surface markers, using monoclonal antibodies capable of binding to specific antigens. In some embodiments, at least 20%, 30%, 40%, 50%, 60%, 70%, 80%, or 85% of the cells of the invention do not express CD133, CD31, CD106, CD146, CD45, CD14, CD117, HLA-DR, or any combination thereof. In some embodiments, at least 5%, 20%, 30%, 40%, 50%, 60%, 70%, 80%, 85%, 90% or 95% of the cells of the invention express CD34, CD58, CD90, CD105, CD29, CD49b, CD49e, CD44, CD49d, HLA-ABC, or any combination thereof. In some embodiments, subsequent methods using antibodies for selection of the cells are pursued for cell isolation, sorting, or a combination thereof. Non-limiting examples of methods well known in the art include flow cytometry, such as fluorescent-activated cell sorting (FACS), magnetic-activated cell sorting (MACS), or others.

In one embodiments, a cell as described herein has a multipotency or a pluripotency differentiation capability. In another embodiment, a cell as described herein expresses the multipotency marker Kruppel-like factor 4 (KLF-4).

As used herein, the term "expresses" or "express" encompassed gene transcription to messenger RNA, translation thereof, or both In one embodiment, a cell of the invention is capable of differentiating into an osteogenic cell. In one embodiment, a cell of the invention is capable of differentiating into an adipocyte. In some embodiments, a cell of the invention is capable of differentiating into a RPE cell. As would be apparent to the skilled artisan, specific stains can be employed for determining cell-specific differentiation process or product thereof. Examples of such stains include, but are not limited to, Alizarin red and Oil red O, for osteogenesis and adipogenesis, respectively. In some embodiments, RPE markers can be used for validating differentiation of a cell of the invention into a RPE cell, non-limiting examples of such marker include: paired box protein-6 (PAX6), orthodenticle homeobox 2 (OTX2), and SIX homeobox 3 (SIX3). As would be apparent to one of ordinary skill in the art, the markers can be used for detection by common methods, such as RT-PCR, qPCR, ELISA, SDS-PAGE, immune-blot, and others.

In some embodiments, a cell of the invention comprises cells in a culture.

In some embodiments, a cell of the invention expresses CXCR4. In some embodiments, at least 50%, 60%, 75%, 85%, 90% or 97% of cells in the culture express CXCR4, or any value and range therebetween. In some embodiments, 20-40%, 30-60%, 15-55%, 40-70%, 60-90%, 65-80%, 70-95%, 85-100% of cells in the culture express CXCR4. Each possibility represents a separate embodiment of the invention.

In some embodiments, a cell of the invention expresses CD73. In some embodiments, at least 50%, 60%, 75%, 85%, 90% or 97% of cells in the culture express CD73, or any value and range therebetween. In some embodiments, 20-40%, 30-60%, 15-55%, 40-70%, 60-90%, 65-80%, 70-95%, 85-100% of cells in the culture express CD73. Each possibility represents a separate embodiment of the invention.

In some embodiment, a cell of the invention expresses CD90. In some embodiments, at least 50%, 60%, 75%, 85%, 90% or 97% of cells in the culture express CD90, or any value and range therebetween. In some embodiments, 20-40%, 30-60%, 15-55%, 40-70%, 60-90%, 65-80%, 70-95%, 85-100% of cells in the culture express CD90. Each possibility represents a separate embodiment of the invention.

In some embodiments, a cell of the invention expresses CD105. In some embodiments, at least 40%, 50%, 60%, 75%, 85%, 90% or 97% of cells in the culture express CD105, or any value and range therebetween. In some embodiments, 20-40%, 30-60%, 15-55%, 40-70%, 60-90%, 65-80%, 70-95%, 85-100% of cells in the culture express CD105. Each possibility represents a separate embodiment of the invention.

In some embodiments, a cell of the invention expresses CD34. In some embodiments, at least 1%, 5%, 10%, 15%, 20%, 30%, 40% or 50% of cells in the culture express CD34, or any value and range therebetween. In some embodiments, 1-10%, 5-15%, 20-25%, 30-40%, 25-45%, 10-30%, 35-50%, 40-60% of cells in the culture express CD34. Each possibility represents a separate embodiment of the invention.

In some embodiments, a cell of the invention expresses CD29. In some embodiments, at least 40%, 50%, 60%, 75%, 85%, 90% or 97% of cells in the culture express CD29, or any value and range therebetween. In some embodiments, 20-40%, 30-60%, 15-55%, 40-70%, 60-90%, 65-80%, 70-95%, 85-100% of cells in the culture express CD29. Each possibility represents a separate embodiment of the invention.

In some embodiment, a cell of the invention does not express CD45.

In some embodiments, at least 97% of cells in the culture express CXCR4, CD73, CD90 and CD105 and 30% of the cells express CD34. In some embodiments, at least 70%, 80%, 90%, 95%, 99% or 100% of cells in the culture do not express CD45. In some embodiments, at least 20%, 30%, 40, or 50% of cells in the culture do not express CD34 and CD45. In some embodiments, at least 20%, 30%, 50%, 60%, 70%, 80%, 90% or 99% of cells in the culture, or any value and range therebetween, express CXCR4, CD34, CD73, CD90, and CD105, and not more than 99%, 90%, 80%, 70%, 60%, 50%, 40%, 30%, 20% or 5% of cells in the culture, or any value and range therebetween, do not express CD45.

As defined herein, the term "cell migration" refers to any process involving the transition of a cell between different sites. In some embodiments, cell migration is characterized by any one of the sub-processes selected from: polarization, protrusion, adhesion, cell body translocation, and retraction of the cell's rear. In one embodiment, cell migration comprises homing. In some embodiments, methods of the present invention increase migration of a cell of the invention. In some embodiments, validating activity comprises determining increased migration of a cell of the invention. In some embodiments, increase is by at least 25%, 50%, 100% or 500%, or any value and range therebetween. In some embodiments, increase is by at least 2-fold, 5-fold, 10-fold or 50-fold. Each possibility represents a separate embodiment of the invention.

Methods of determining homing, adhesion, and migration are common, and any known method may be used for validating such activity. Non-limiting examples of such methods include: Boyden Chamber assays, scratch assays, cell-exclusion zone assays, and microfluidic based assays. In one embodiment, increase in cell migration includes increasing migration speed. In one embodiment, increase in cell migration includes increasing migration distance. In one embodiment, increase in cell migration includes increasing the number of migratory cells. In one embodiment, increase in cell migration includes increasing the average migration speed of the cells within the composition. In one embodiment, increase in cell migration includes increasing the average migration distance of cells within the composition.

As used herein, "CXCR4" refers to a polypeptide that binds to stromal-derived-factor-1 (SDF-1). In one embodiment, CXCR4 is a SDF-1 receptor. In one embodiment, CXCR4 is Fusin. In another embodiment, CXCR4 is a leukocyte-derived seven-transmembrane domain receptor (LESTR). In some embodiments, a cell of the invention expresses CXCR4. In some embodiments, methods for obtaining a cell composition of the invention include increasing CXCR4 expression of the cells by at least 5%, 20%, 50%, 100%, 200%, 300%, or 500%, or any value and range therebetween. In some embodiments, methods for obtaining a cell composition of the invention include increasing CXCR4 expression by at least 2-fold, 5-fold, 10-fold, 25-fold or 50-fold, or any value and range therebetween. Methods for detecting CXCR4 expression are common and would be apparent to one of ordinary skill in the art. Non-limiting examples include detection at the transcript and protein levels, such as by, PCR (e.g., RT-PCR, qRT-PCR), ELISA, etc.

As used herein, the term "anti-inflammatory cytokine" refers to any immunoregulatory molecule that controls, promotes, increases, enhances, propagates, or any combination thereof, a proinflammatory cytokines response. In some embodiments, methods of the present invention increase expression of anti-inflammatory cytokines by a cell of the invention. In some embodiments, anti-inflammatory cytokines are selected from: interleukin (IL)-1 receptor antagonist, IL-4, IL-10, IL-11, IL-13, Leukemia inhibitory factor (LIF), interferon-alpha (INF-α), IL-6, and transforming growth factor (TGF)-β. In one embodiment, IL-1R, TNF-αR, and IL-18R also inhibit proinflammatory cytokines. In some embodiments, performing methods of the invention results in increased expression of the cytokine macrophage inflammatory protein-3-beta (MIP-3-beta). In one embodiment, MIP-3-beta is Chemokine (C—C motif) ligand 19. In some embodiments, performing the methods of the invention results increased expression of insulin-like growth factor binding protein 6 (IGFBP-6).

As used herein, the term "neurotrophic cytokine" refers to a group of polypeptides which are secreted predominantly by neuronal cells and are known to induce, promote, or increase survival of cells and their proper function and development. In some embodiments, performing the methods of the invention results in increased expression of neurotrophic cytokines by a cell of the invention. In some embodiments, a neurotrophic cytokine is selected from: hepatocyte growth factor (HGF), nerve growth factor (NGF), brain derived neurotrophic factor (BDNF), neurotrophin-3 (NT-3), neurotrophin-4 (NT-4), neurotrophin-6 (NT-6), neurotrophin-7 (NT-7), glial cell line-derived neurotrophic factor (GDNF), neurturin (NRTN), artemin (ARTN), persephin (PSPN), and Cillian neurotrophic factor (CNTF).

The presence or level of any one of anti-inflammatory or neural cytokines, in a biological sample can be determined using any method known in the art. Non-limiting examples include antibody arrays, spectroscopy, column chromatography; HPLC; FPLC; matrix-affinity chromatography; reverse-phase chromatography; optical spectroscopic techniques; electrophoretic separation, qPCR, RT-PCR; and others.

As used herein, the term "retinal pigment epithelium (RPE) layer" refers to the pigmented cell layer outside the neurosensory retina that nourishes retinal visual cells and is firmly attached to the underlying choroid and overlying retinal visual cells. In some embodiments, degeneration comprises detachment. In some embodiments, degeneration comprises apoptosis. In some embodiments, degeneration comprises necrosis. In some embodiments, RPE degeneration is induced by stress. In some embodiments, stress comprises oxidative stress. In some embodiments, oxidative stress is a result of poor circulation. In some embodiments, poor circulation is associated with age. In some embodiments, RPE degeneration induced by oxidative stress is a symptom of an age-related disease or disorder.

In some embodiments, the present invention is directed to methods comprising contacting RPE cells with a cell of the invention for treating or preventing RPE degeneration in a subject. In some embodiments, a cell composition of the invention is administrated for increasing Müller cell activation in the retina. In some embodiments, a cell composition of the invention is administrated for increasing retinal intactness. In some embodiments, a cell composition of the invention is administrated for increasing Microglia activation and migration into the retina. In some embodiments, a cell composition of the invention is administrated for increasing cell proliferation in the choroid of the eye. In some embodiments, a cell composition of the invention is administrated for reducing the thinning of the outer nuclear layer (ONL). In some embodiments, a cell composition of the invention is administrated for increasing ONL thickening. In some embodiments, a cell composition of the invention is administrated for increasing the size of the photoreceptor layer. In some embodiments, a cell composition of the invention is administrated for increasing expression of rhodopsin. In some embodiments, administration of a cell composition of the invention comprises a sub-retinal injection to a subject in need thereof. As would be apparent to one of ordinary skill in the art, RPE healthy morphology is characterized by staining of structural or neural markers using antibodies. Non-limiting examples of such markers include GFAP, RPE65, Iba1, Ki67, rhodopsin, and others.

As used herein, the term "scaffold" refers to a structure or a composition carrying cells and comprising a biocompatible material that provides a surface suitable for adherence/attachment, maturation, differentiation, and proliferation of cells. In one embodiment, a scaffold may further provide mechanical stability and support. In one embodiment, a scaffold may be in a particular shape or form so as to influence or delimit a three-dimensional shape or form assumed by a population of proliferating cells. Three-dimensional shapes may include: films, ribbons, cords, sheets, flat discs, cylinders, spheres, 3-dimensional amorphous shapes, etc.

As used herein, the term "biocompatible" refers to the ability of an object to be accepted by and to function in a recipient without eliciting a significant foreign body response (such as, for example, an immune, inflammatory, thrombogenic, or the like response). For example, when used with reference to one or more of the polymeric materials of the invention, biocompatible refers to the ability of the polymeric material (or polymeric materials) to be accepted by and to function in its intended manner in the recipient.

The scaffold, in one embodiment, is a porous matrix. In one embodiment, the porous scaffold comprises at least 50% porosity. In another embodiment, the porous scaffold comprises at least 60% porosity, at least 70% porosity, at least 75% porosity, at least 80% porosity, at least 85% porosity, at least 90% porosity, at least 92% porosity, or at least 95% porosity, or any value and range therebetween. In one embodiment, the porous scaffold comprises 50-70% porosity, 60-80% porosity, 65-85% porosity, 75-90% porosity, or 88-95% porosity. Each possibility represents a separate embodiment of the invention.

In another embodiment, the porous scaffold comprises pores having a diameter of at least 100 μm. In another embodiment, the porous scaffold comprises pores having a diameter of at least 120 μm. In another embodiment, the porous scaffold comprises pores having a diameter of at least 150 μm. In another embodiment, the porous scaffold comprises pores having a diameter of 100-900 μm. In another embodiment, the porous scaffold comprises pores having a diameter of 120-900 μm. In another embodiment, the porous scaffold comprises pores having a diameter of 120-850 μm. In another embodiment, the porous scaffold comprises pores having a diameter of 150-800 μm. In another embodiment, the porous scaffold comprises pores having a diameter of 200-800 µm. In another embodiment, the porous scaffold comprises pores having a diameter of 220-750 µm.

In another embodiment, the scaffold (e.g., matrix) is devoid of any one of an organized structure, layer, or network of layers. In another embodiment, the composition is devoid of any layer of aligned fibers. In another embodiment, the scaffold is devoid of any layer of aligned fibers. In another embodiment, the composition is devoid of curved fibers. In another embodiment, the scaffold is devoid of curved fibers.

In another embodiment, a composition as described herein is cultured for at least 14 days in-vitro or ex-vivo, in order to reach baseline proliferation rates.

In another embodiment, the cell is attached to a scaffold such as described herein for at least 7 days. In another embodiment, the cell is attached to a scaffold such as described herein for at least 14 days. In another embodiment, the cell is attached to a scaffold such as described herein for 7 to 21 days. In another embodiment, the cell is attached to a scaffold such as described herein for 14 to 31 days. In another embodiment, the cell is attached to a scaffold such as described herein for 30 to 60 days. In another embodiment, the cell is attached to a scaffold such as described herein for 25 to 75 days. In another embodiment, the cell is attached to a scaffold such as described herein for 50 to 90 days.

In another embodiment, the present invention is further directed to a composition that is cultured for at least 7 days. In another embodiment, the present invention is further directed to a composition that is cultured for at least 14 days. In another embodiment, the present invention is further directed to a composition that is cultured for at least 21 days. In another embodiment, the present invention is further directed to a composition that is cultured for at least 28 days. In another embodiment, the present invention is further directed to a composition that is cultured for at least 3 months days.

In another embodiment, the porous scaffold is further coated with a polymer. In another embodiment, the porous scaffold is further coated with an extracellular matrix protein. In another embodiment, the porous scaffold is further coated with fibronectin. In another embodiment, the porous scaffold is further coated with polypyrrole. In another embodiment, the porous scaffold is further coated with polycaprolactone. In another embodiment, the porous scaffold is further coated with poly(ethersulfone). In another embodiment, the porous scaffold is further coated with poly(acrylonitrile-co-methylacrylate) (PAN-MA). In another embodiment, the porous scaffold further comprises a chemoattractant such as, but not limited to, laminin-1.

In another embodiment, a composition as described herein further comprises fibrin. In another embodiment, a composition as described herein further comprises thrombin.

In another embodiment, a scaffold such as described herein is 10-160 mm$^3$. In another embodiment, a scaffold such as described herein is 10-80 mm$^3$. In another embodiment, a scaffold such as described herein is 15-50 mm$^3$.

In another embodiment, the scaffolds described herein can further include a therapeutic agent (e.g., suitable for treating a subject afflicted with a damaged RPE). In another embodiment, the therapeutic agent can be any therapeutic agent. In another embodiment, the therapeutic agent can be a polypeptide, polypeptide fragment, nucleic acid molecule, small molecule, ribozyme, short hairpin RNA (shRNA), RNA interference (RNAi), antibody, antibody fragment, scFv, enzyme, carbohydrate, or any combination thereof. In one embodiment, a scaffold as described herein can release the therapeutic agent for at least 1 day, 1 week, or 1 month.

In another embodiment, a composition as described herein further comprises a material selected from: collagen-GAG, collagen, fibrin, PLA, PGA, PLA-PGA co-polymer, poly(anhydride), poly(hydroxy acid), poly(ortho ester), poly(propylfumerate), poly(caprolactone), polyamide, polyamino acid, polyacetal, biodegradable polycyanoacrylate, biodegradable polyurethane and polysaccharide, polypyrrole, polyaniline, polythiophene, polystyrene, polyester, nonbiodegradable polyurethane, polyurea, poly(ethylene vinyl acetate), polypropylene, polymethacrylate, polyethylene, polycarbonate, and poly(ethylene oxide).

In another embodiment, a composition as described herein further comprises a cell adhesion promoting agent, a proliferation inducer, a differentiation inducer, an extravasation inducer, a migration inducer, or any combination thereof. In another embodiment, a composition as described herein further comprises a cell adhesion protein, a growth factor, a cytokine, a hormone, a protease a protease substrate, or any combination thereof. In another embodiment, any substance as described herein is attached to the scaffold. In another embodiment, any substance as described herein is embedded within the scaffold. In another embodiment, any substance as described herein is impregnated within the scaffold. In another embodiment, a scaffold such as described herein is coated with a gel. In another embodiment, a scaffold such as described herein is biodegradable.

In another embodiment, the porosity of the scaffold is controlled by a variety of techniques known to those skilled in the art. In another embodiment, as the porosity is increased, use of polymers having a higher modulus, addition of suffer polymers as a co-polymer or mixture, or an increase in the cross-link density of the polymer are used to increase the stability of the scaffold with respect to cellular contraction.

In another embodiment, the choice of polymer and the ratio of polymers in a co-polymer scaffold is adjusted to optimize the stiffness/porosity of the scaffold. In another embodiment, the molecular weight and cross-link density of the scaffold is regulated to control both the mechanical properties of the scaffold and the degradation rate (for degradable scaffolds). In another embodiment, the mechanical properties are optimized to mimic those of the tissue at the implant site. In another embodiment, the shape and size of the final scaffold are adapted for the implant site and tissue type. In another embodiment, scaffold materials comprise natural or synthetic organic polymers that can be gelled, or polymerized or solidified (e.g., by aggregation, coagulation, hydrophobic interactions, or cross-linking) into a hydrogel e.g., structure that entraps water and/or other molecules.

In another embodiment, polymers used in scaffold material compositions are biocompatible, biodegradable and/or bioerodible and act as adhesive substrates for cells. In another embodiment, the structural scaffold materials are non-resorbing or non-biodegradable polymers or materials. The phrase "non-biodegradable polymer", as used herein, refers to a polymer or polymers which at least substantially (i.e. more than 50%) do not degrade or erode in-vivo. The terms "non-biodegradable" and "non-resorbing" are equivalent and are used herein interchangeably.

In another embodiment, the phrase "biodegradable polymer" as used herein, refers to a polymer or polymers which degrade in-vivo, and wherein erosion of the polymer or polymers over time occurs concurrent with or subsequent to release of cells/tissue. The terms "biodegradable" and "bioerodible" are equivalent and are used herein interchangeably.

In another embodiment, scaffold materials comprise naturally occurring substances, such as, fibrinogen, fibrin, thrombin, chitosan, collagen, alginate, poly(N-isopropylacrylamide), hyaluronate, albumin, collagen, synthetic polyamino acids, prolamines, polysaccharides such as alginate, heparin, and other naturally occurring biodegradable polymers of sugar units. In another embodiment, structural scaffold materials are ionic hydrogels, for example, ionic polysaccharides, such as alginates or chitosan. Ionic hydrogels may be produced by cross-linking the anionic salt of alginic acid, a carbohydrate polymer isolated from seaweed, with ions, such as calcium cations.

In another embodiment, a scaffold can be made by any of a variety of techniques known to those skilled in the art. Salt-leaching, porogens, solid-liquid phase separation (sometimes termed freeze-drying), and phase inversion fabrication are used, in some embodiments, to produce porous scaffolds.

As used herein, "transplanting" refers to providing the scaffold supported cells of the present invention, using any suitable route, as known to one skilled in the art. Typically, the scaffold-supported cells are administered by injection using a catheter.

Compositions

According to some embodiments, the invention is directed to a pharmaceutical composition comprising as an active ingredient a therapeutically effective amount of a mesenchymal cell of the present invention, and a pharmaceutically acceptable carrier and/or diluent. In some embodiments, the pharmaceutical composition facilitates administration of a cell of the invention to the target tissue.

According to another embodiment, a use of the composition of the invention for preparation of a medicament for treating age-related ophthalmic disease is provided.

As used herein, the term "carrier", "adjuvant" or "excipient" refers to any component of a pharmaceutical composition that is not a cell or a cytokine. As used herein, the term "carrier" includes cell culture media.

As used herein, the term "pharmaceutically acceptable" means suitable for administration to a subject, e.g., a human and/or for growing, differentiating and/or propagating a cell as described herein. For example, the term "pharmaceutically acceptable" can mean approved by a regulatory agency of the Federal or a state government or listed in the U.S. Pharmacopeia or other generally recognized pharmacopeia for use in animals, and more particularly in humans. In some embodiments, pharmaceutically acceptable carrier is non-toxic, inert solid, semi-solid liquid filler, diluent, encapsulating material, formulation auxiliary of any type, or simply a sterile aqueous medium, such as saline. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents that may be useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety.

According to an embodiment of the invention, pharmaceutical compositions contain 0.1%-95% of cells of the present invention. According to another embodiment of the invention, pharmaceutical compositions contain 1-70% cells. According to another embodiment of the invention, the composition or formulation to be administered may contain a quantity of cells, according to embodiments of the invention in an amount effective to treat the condition or disease of the subject being treated.

According to one embodiment, the compositions of the invention are administered in the form of a pharmaceutical composition comprising at least one of the active components of this invention (the cells) together with a pharmaceutically acceptable carrier or diluent. In another embodiment, the compositions of this invention can be administered either individually or together in any conventional subretinal or transdermal dosage form.

The carrier may comprise, in total, from about 0.1% to about 99.99999% by weight of the pharmaceutical compositions presented herein.

The composition also includes incorporation of the active material into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

As used herein, the terms "administering," "administration," and like terms refer to any method which, in sound medical practice, delivers a composition containing an active agent to a subject in such a manner as to provide a therapeutic effect.

In one embodiment, depending on the severity and responsiveness of the condition to be treated, dosing can be of a single or a plurality of administrations, with course of treatment lasting from several days to several weeks or until cure is affected or diminution of the disease state is achieved.

As used herein, the term "therapeutically active molecule" or "therapeutic agent" means a molecule, group of molecules, complex or substance administered to an organism for diagnostic, therapeutic, preventative medical, or veterinary purposes. This term includes pharmaceuticals, e.g., small molecules, treatments, remedies, biologics, devices, and diagnostics, including preparations useful in clinical screening, prevention, prophylaxis, healing, imaging, therapy, surgery, monitoring, and the like. This term can also specifically include nucleic acids and compounds comprising nucleic acids that produce a bioactive effect, for example.

The term "therapeutically effective amount" refers to the concentration of cells that: (a) express CXCR4, CD73, CD90, CD105, or any combination thereof; and (b) lack expression of CD34, CD45, or their combination, normalized to body weight, that is effective to treat a disease or disorder in a mammal. The term "a therapeutically effective amount" refers to an amount effective, at dosages and for periods of time necessary, to achieve the desired therapeutic or prophylactic result. A physician or veterinarian of ordinary skill can readily determine and prescribe the effective amount of the bioactive agent required.

In some embodiments, a composition of the invention comprises pharmaceutically active agents. In some embodiments, pharmaceutically active agents are added prior to transplantation. Pharmaceutically active agents include but are not limited to any of the specific examples disclosed herein. Those of ordinary skill in the art will recognize also numerous other compounds that fall within this category and are useful according to the invention.

As used herein, the terms "therapeutically active molecule" or "therapeutic agent" means a molecule, group of molecules, complex or substance administered to an organism for diagnostic, therapeutic, preventative medical, or veterinary purposes. These terms include pharmaceuticals, e.g., small molecules, treatments, remedies, biologics, devices, and diagnostics, including preparations useful in clinical screening, prevention, prophylaxis, healing, imaging, therapy, surgery, monitoring, and the like. These terms can also specifically include nucleic acids and compounds comprising nucleic acids that produce a bioactive effect, for example.

Use of the Compositions

According to some embodiments, a method for treating, ameliorating, reducing and/or preventing a condition associated with damaged retinal pigment epithelium (RPE) in a subject in need thereof, the method comprising the step of: administering to a subject a pharmaceutical composition comprising an effective amount of the cells of the invention, thereby treating, ameliorating, reducing and/or preventing a condition associated with damaged retinal pigment epithelium (RPE) in the subject in need thereof, is provided. In some embodiments, a disease associated with damaged RPE is selected from: age-related macular degeneration (AMD), dry AMD, wet AMD, retinal detachment, retinal pigmentosa, refractive errors, cataracts, and diabetic retinopathy.

As used herein, "age-related macular degeneration (AMD)" is the most common cause of irreversible central vision loss in elderly patient. AMD can be detected by any method known in the art. Non-limiting examples include: funduscopic examination, color fundus photography, fluorescein angiography, optical coherence tomography, or other.

According to some embodiments, a method for treating, ameliorating, reducing and/or preventing age-related macular degeneration (AMD) in a subject in need thereof, the method comprising the step of: administering to a subject a pharmaceutical composition comprising an effective amount of the cells of the invention, thereby treating, ameliorating, reducing and/or preventing age-related macular degeneration (AMD) in a subject in need thereof, is provided.

As used herein, the terms "treat," "treating," "treatment," and the like refer to reducing or ameliorating a disease or condition, e.g., diabetes, hyperglycemia, insulin resistance, and/or symptoms associated therewith. Moreover, treatment includes the partial or complete regeneration of retinal pigment epithelium activity in a subject. It will be appreciated that, although not precluded, treating a disease or condition does not require that the disease, condition, or symptoms associated therewith be completely eliminated.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

The terms "subject" or "patient" refer to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

In one embodiment, a cell of the present invention is provided to the subject per se. In one embodiment, a cell of the present invention is provided to the subject as part of a pharmaceutical composition where it is mixed with a pharmaceutically acceptable carrier. In some embodiments, a provided cell of the invention is autotransplanted. As defined herein, the term "autotransplantation" refers to transplantation of any one of organs, tissues, or cells from the same person. In one embodiment, an autologous tissue transplanted by autotransplantation is referred to as an autograft or autotransplant. In some embodiments, a provided cell of the invention is allotransplanted. As defined herein, the term "allotransplantation" refers to transplantation of organs, tissues, or cells to a recipient of the same species but from a genetically non-identical donor. In one embodiment, an allogeneic tissue transplanted by allotransplantation is referred to as an allograft or allogeneic transplant.

In some embodiments, the invention is directed to methods of activating a cell of the invention. In some embodiments, methods of the invention comprise providing oxidative stress to a RPE cell. In one embodiment, oxidative stress induction includes, but not limited to, contacting a RPE cell with hydrogen peroxide ($H_2O_2$) or sodium iodate ($NaIO_3$). In some embodiments, oxidative stress treatment to a RPE cell is for at least 8 hours, 16 hours, 24 hours, 3 days, 1 week or 1 month, or any range and value therebetween. In some embodiments, the culture medium of oxidative stress treatment to a RPE cell is collected or preserved by methods including, but not limited to centrifugation, phase separation, snap-freezing, freezing by liquid nitrogen, or any other method known in the art. In some embodiments, methods of activating a cell of the invention comprise the step of contacting the cell with an oxidatively-stressed RPE cell. In some embodiments, methods of activating a cell of the invention comprise the step of contacting the cell with freshly collected or preserved culture medium of an oxidatively-stressed RPE cell. In some embodiments, a cell of the invention is co-cultured with an oxidatively-stressed RPE cell or cultured with freshly collected or preserved culture medium derived from an oxidatively-stressed RPE cell for at least 2 days, 3 days, 5 days or 7 days, or any range and value therebetween. In some embodiments, a cell of the invention is co-cultured with an oxidatively-stressed RPE cell or cultured with freshly collected or preserved culture medium derived from an oxidatively-stressed RPE cells and is used in a method of preparing a therapeutic AMD cell composition.

In some embodiments, a therapeutic AMD cell composition is provided. In some embodiments, therapeutic AMD cell composition comprises a cell of the invention activated by co-culturing with an oxidatively-stressed RPE cell or culturing with freshly collected or preserved culture medium derived from an oxidatively-stressed RPE cells. In some embodiments, therapeutic AMD cell culture comprises an activated cell of the invention in composition with any acceptable carrier.

As used herein, the term "prevention" of a disease, disorder, or condition encompasses the delay, prevention, suppression, or inhibition of the onset of a disease, disorder, or condition. As used in accordance with the presently described subject matter, the term "prevention" relates to a process of prophylaxis in which a subject is exposed to the presently described cells prior to the induction or onset of the disease/disorder process. This could be done where an individual has a genetic pedigree indicating a predisposition toward occurrence of the disease/disorder to be prevented. For example, this might be true of an individual whose ancestors show a predisposition toward certain types of, for example, inflammatory disorders. The term "suppression" is used to describe a condition wherein the disease/disorder process has already begun but obvious symptoms of the condition have yet to be realized. Thus, the cells of an individual may have the disease/disorder, but no outside signs of the disease/disorder have yet been clinically recognized. In either case, the term prophylaxis can be applied to encompass both prevention and suppression. Conversely, the term "treatment" refers to the clinical application of active agents to combat an already existing condition whose clinical presentation has already been realized in a patient.

As used herein, the term "condition" includes anatomic and physiological deviations from the normal that constitute an impairment of the normal state of the living animal or one of its parts, that interrupts or modifies the performance of the bodily functions.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as polymer subunits, size or thickness, are to be understood to include any integer within the recited range, unless otherwise indicated.

In one embodiment, any "increase", "decrease", a synonym thereof, or change related to a cell as described herein is relative to MSC derived from fat. In one embodiment, any "increase", "decrease", or change related to a cell as described herein is relative to MSC derived from fat of an adult human. In one embodiment, any "increase", "decrease", or change related to a cell as described herein is relative to MSC within a primary cell-culture, wherein the MSC is derived from fat of an adult human.

As used herein, the terms "subject" or "individual" or "animal" or "patient" or "mammal," refer to any subject, particularly a mammalian subject, for whom therapy is desired, for example, a human.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Materials and Methods

The purpose of the study and the procedures to be used were presented to all of the subjects, and a signed informed consent was obtained from each. This study was approved by the ethics committee for clinical trials of Tel Aviv Sourasky Medical Center, and the procedures used conformed to the tenets of the Declaration of Helsinki.
Isolation, Characterization and Culture of Adipose-Derived Mesenchymal Stem Cell (ASC)
Isolation and Culture of Human Adipose Tissue-Derived Stem Cells (ASCs)

Human adipose tissue was harvested from 5 healthy patients with a mean age of 38±4.3 years and body mass index of 28.2±3.9 who had abdominoplasty for aesthetic reasons at Tel Aviv Sourasky Medical Center. No metabolic diseases, HIV, hepatitis, or other systemic complications were reported from these patients.

The isolation and culture of ASCs was performed as follows: 60 to 120 ml of the raw lipoaspirates were washed with phosphate-buffered saline (PBS) and enzymatically digested with 0.75% collagenase type I (Cat. no. C1639, Sigma) at 37° C. for 1 hour. The digested lipoaspirates were centrifuged at 400 g for 15 minutes, and the pellet was resuspended and passed through a 100-μm mesh filter (Cat. no. 542000, EASYstrainer, Greiner bio-one) to remove debris. Subsequently, $1 \times 10^6$ cells were plated in 100-mm culture dishes in ADSC medium and incubated at 37° C. in a humidified 8% $CO_2$ atmosphere. The medium was changed twice weekly, and cells were passaged with 0.25% trypsin/0.1% EDTA (Biological Industries, Israel) upon reaching 90% confluency. Experiments were performed at passage 3-4.

Characterization of ASCs for Mesenchymal Stem Cells (MSCs) Markers by Immunostaining and FACS Analysis Characterization of cultured ASCs was performed at passage three as follows; after reaching 100% confluence, cells were trypsinized, and collected to FACS tubes in aliquots ($10^5$ cells/tube). Cells were then stained with fluorescein isothiocyanate (FITC) and phycoerythrin (PE) conjugated monoclonal antibodies against human CD45 (Dako), CD90 (Dako), CD105 (ebioscience), CD73 (BD pharmingen). Cells were subsequently analyzed by FACS Cantoll flow cytometer (BD Biosciences). Isotype-matched FITC and PE conjugated antibodies, were used as controls.
Multipotency of ASCs by Differentiation to Osteocytes and Adipocytes ASCs at passage 3 were studied for their ability to differentiate to osteocytes and adipocytes. Cells were seeded in a 24 well plate at a density of $1 \times 10^4$ cells per well. At confluency of 100%, differentiation media was added to the cells and changed twice a week (adipose: 10% FBS, 1 μM dexamethasone, 0.5 mM 3-isobutyl-1-methylxanthine, 10 μg/mL insulin and 100 μM indomethacin in high glucose (HG)-DMEM. Bone: stem pro® osteocyte differentiation basal medium (Gibco). Protocol lasted either two or three weeks to induce bone and adipose differentiation, respectively.

Differentiation to adipocytes was assessed using an Oil Red O stain as an indicator of intracellular lipid accumulation. The cells were fixed for 20 min at room temperature in 4% paraformaldehyde. Cells were incubated in 0.5% (w/v) Oil Red O reagent in 100% Isopropanol (Sigma) for 10 min at room temperature. Excess stain was removed by washing with distilled water.

Bone differentiation was assessed using Alizarin red (Sigma). Cells were fixated with 4% paraformaldehyde for 20 min and then stained with Alizarin red 2% solution adjusted to pH 4.2, for 15 min at room temperature. Excess stain was removed by washing with several changes of distilled water.

Images of stained cells with both Oil Red O and Alizarin red were taken by light microscopy. Results are presented as the percent of stained cells from the total number of cells counted in a high-power field.
Primary RPE Culture Human pRPE cells ($5.5 \times 10^5$ cells; Lonza) were plated in 100-mm culture dishes (Falcon) in RtEGM Bulletkit medium (Lonza) and incubated at 37° C. in a humidified 5% $CO_2$ atmosphere. The medium was replaced twice weekly, and cells were passaged with 0.25% trypsin/0.1% EDTA (Biological Industries, Israel) upon reaching 90% confluence. Experiments were performed at passage 3-4.
Scratch Assay
Oxidative Stress Induction RPE cells were seeded at $1 \times 10^4$ cells/cm$^2$ in RtEGM medium containing 2% FBS (Lonza). After adhesion of the cells to the dish, the medium was changed to free-FBS RtEGM and renewed every two days until treatments were initiated. To induce oxidative stress, sub-confluent RPE cells were treated for 16 h with 0.5 mM $H_2O_2$ (Cat. no. 216763, Sigma) in ADSC serum free medium, after which the medium was collected and centrifuged at 1,500 rpm for 5 min.
Scratch Assay ASCs were seeded in 6 well plates (falcon) until confluence. Cells were cultured in ADSC serum free conditions and the monolayers were then scored with a sterile pipette tip to leave a scratch. Culture medium was immediately removed along with any detached cells and replaced with either fresh ADSC serum free medium (non-CM), conditioned medium of RPE cells treated with $H_2O_2$ (stressed RPE-CM) or conditioned medium of RPE cells without $H_2O_2$ (RPE-CM). All scratch assays were performed in quadruplicates and images were taken at the beginning of the treatments (time zero) and after 24 h ($H_2O_2$ treatments). ASCs cells as well as RPE cells were then harvested for mRNA analysis by qRT-PCR.

Rescue Studies

Preparation of ASCs Conditioned Medium

ASCs ($1\times10^6$ cells/cm$^2$) at passage 3 or passage 5 were seeded on a 100 mm dish (Falcon) and cultured in ADSC BulletKit™ Medium (Lonza). At 100% confluence, ASCs were washed with PBS×1 and cultured with ADSC serum free medium (Lonza) for 48 h. Medium was collected, filtered using a 0.22 mm syringe filter and was either immediately transferred to RPE cells or maintained in −80° C. for further protein analysis using ELISA assay. In turn ASC cells were harvested for mRNA level detection using RT-PCR. ASCs at passage 5 showed aspects of senescence evident by low proliferation rate and morphology changes (data not shown). The condition medium of ASCs at passage 5 (P5-CM) was used in this study as negative control to the condition medium collected from ASCs at passage 3 (P3-CM).

RPE Pre-Incubation with ASCs'-CM Followed by Treatment with $H_2O_2$

RPE cells were seeded as described above in a 6 well plate (Falcon), after reaching approximately 90% confluence RPE cells were pre-incubated for 48 h with either conditioned medium from ASCs at passage 3 (P3-CM), conditioned medium from ASCs at passage 5 (P5-CM) or with non-conditioned, ADSC serum free medium (non-CM) as control. RPE cells were then washed with PBS×1 followed by exposure to 1 mM $H_2O_2$ or without $H_2O_2$ as a control. After 7 h, RPE cell death was monitored by propidium iodide (PI) using FACS analysis and by Ethidium bromide and Acridine orange fluorescent staining.

Propidium Iodide Staining and Flow Cytometry Analysis

Following rescue studies as described above, RPE cells ($3\times10^5$) at passage 3 were harvested with 0.25% trypsin/EDTA (Biological Industries). Cells were collected by centrifugation at 500 g for 5 min, washed twice with phosphate-buffered saline (PBS), and re-suspended in 400 µl of PBS to which 1 µl of propidium iodide (Sigma) 1 mg/ml was added immediately before flow cytometry measurements. At least 10,000 events were collected and labeled, fluorescence cells were detected by BD FACS Canto™ II cytometer (BD Pharmingen, USA). Analysis of cell death distribution was conducted by FCS Express 4 software (De Novo Software, Canada).

Ethidium Bromide and Acridine Orange Fluorescent Staining

Following rescue studies as described above, RPE cells were collected by trypsinization, the apoptosis and necrosis rate of RPE was assessed using Ethidium bromide and Acridine orange fluorescent staining as follows: Fluorescent staining solution (0.5 µl) containing an equal volume of 100 µg/ml Acridine orange and 100 µg/ml Ethidium bromide (Sigma) were added to each cell suspension sample, and then covered with a coverslip. $1.5\times10^4$ cells were counted, and the morphology of cell death was examined and analyzed immediately at room temperature.

Quantitative RT-PCR

Total RNA was extracted from ASCs or RPE cell cultures using High Pure RNA Isolation Kit (Roche) according to the manufacturer's instructions. Total RNA concentration was determined by NanoDrop™ 1000 Spectrophotometer (Thermo Scientific) and was reverse transcribed using Verso cDNA synthesis kit (Thermo-Scientific). The mRNA expression levels of the growth factors: hepatocyte growth factor (HGF), vascular endothelial growth factor (VEGF), interleukin-1β (IL-1β), stromal-derived factor (SDF), the chemokine receptor CXCR4 and normalizing housekeeping genes GUSB and RLP27 were measured by real-time reverse transcription polymerase chain reaction (RT-PCR) (StepOnePlus—Applied Biosystems), using SYBR® Green qPCR Mastermix (Qiagen). The cycling RT-PCR conditions were as follows: 10 min at 95° C., 40 cycles for 10 s at 95° C., 15 s at 60° C., followed by gradient stage from 60 to 95° C. to obtain a melting curve. The results were calculated by the ΔΔCT method of relative quantitation.

Enzyme-Linked Immunosorbent Assay (ELISA)

Conditioned media was prepared as described above. Briefly ASCs' medium was changed to serum-free medium, following 48 h of incubation medium was collected and centrifuged at 2,500 rpm for 5 min and stored at −80° C. until they were assayed. Levels of HGF were measured by ELISA according to manufacturer protocols (HGF, R&D Systems) results were compared to control group comprising senescent ASCs evident by high passage, phenotype and low proliferation.

Isolation of Orbital Fat-Derived Mesenchymal Stem Cell (OMSC)

Orbital adipose tissue was harvested from three patients between 57-81 years of age who went through blepharoplasty in the Ophthalmology Department Tel Aviv medical center. Due to the lack of fat tissue, the inventors included in the research older and sicker patients than intended. Anemia, lipid metabolic disorder, chronic obstructive pulmonary disease, hypertension, mycosis fungoides, glaucoma, diabetic mellitus II, and diabetic retinopathy were some of the medical conditions the patients suffered from. Stem cells were purified by subjecting orbital fat to collagenase digestion. Suspended cells were plated on 10 cm tissue culture plates.

Maintaining OMSC in Culture

Harvested OMSCs were cultured and expanded in vitro. Human RPE cells were purchased from an external supplier and were cultured as well. OMSCs and RPE cells were subcultured until they reached passage three.

Characterization of OMSC

At day seven post isolation, OMSCs were analyzed for the expression of mesenchymal stem cell markers from adipose tissue by immunostaining and FACS analysis. OMSCs were assayed for CD73, CD105, CD90, CD45 and CD34.

Introducing Fluorescent Staining Dye into Cells

Each cell line was marked with a different fluorescent dye in order to lineage-trace differentiated cells following co-culture. OMSCs were stained with green fluorescent dye using carboxyfluorescein succinimidyl ester (CFSE) and RPE were stained with violet fluorescent dye using cell trace violet proliferation kit.

Evaluation of the Differentiation Capacity of OMSCs to RPE Using a Co-Culture System One million ($1\times10^6$) green fluorescent stained OMSCs were co-cultured with $1\times10^6$ ultra violet stained primary human RPE cells for one week in order to induce stem cell differentiation to RPE. After a week, the co-culture was harvested, and cells were sorted by FACS for segregation to two populations: OMSCs and RPE based on the previously mentioned staining. mRNA was extracted from purified OMSCs and converted into cDNA. qRT-PCR was conducted for the following markers (using the following primer sequences): Pluripotency marker: Klf-4 forward and reverse oligonucleotides. Early neural marker: Otx2—F: 5'-TAAGCCTAGCAGTAAAGAGACATTGG-3' (SEQ ID NO: 1) and R: 5'-TAACATCTGCAAGCATAAACGACAA-3' (SEQ ID NO: 2). Early eye field markers: Pax6—F: 5'-ACGGCTGCCTTGCCTTCT-3' (SEQ ID NO: 3) and R: 5'-CTGGAGCTCTGTTTGGAAGGA-3' (SEQ ID NO: 4); Six3—F: 5'-CCGGAAGAGTTGTCCATGTT-3' (SEQ ID NO: 5) and R: 5'-CTCCTCCAGCGTCTCACAG-3' (SEQ ID NO: 6). RPE marker: RPE65—F: 5'-ACCACAGAAGGTTCATCCGC (SEQ ID NO: 7) and R: 5'-CAGGGATCTGGGAAAGCACA-3' (SEQ ID NO: 8).

cDNAs were quantified using qRT-PCR in order to evaluate differentiation. Results were compared to two control groups, which were cultured in parallel to the co-culture system: (1) Negative control—OMSCs that were marked with CSFE and were not co cultured with RPE, and (2) Positive control—mature RPE.

Sub-Retinal Treatment with ASCs Following NaIO$_3$-Induced Damage to Mice Eyes

Adult C57BL mice received 50 mg/kg of NaIO$_3$ systemically with an IP injection. Three (3) days later the left eye of each mouse received treatment via sub-retinal injection. The experiment group was injected with adipose-derived stem cells (NaIO$_3$+ASC) and the control group received PBS injection (NaIO$_3$+PBS). The right eyes were exposed to NaIO$_3$ but did not undergo any treatment (NaIO$_3$ only). Seven (7) days following treatment both eyes were enucleated, fixed and frozen for immunohistochemical analysis.

Example 1

Phenotypic Characterization and Multipotency of ASCs

ASCs were isolated from lipoaspirate of subcutaneous fat of donors. Phenotypic characterization was studied at passage 3 using immunostaining and FACS analysis. ASCs expressed classic MSCs markers (CD90: 100±1.98%; CD73: 97±5.2%; CD105: 97.8±1.7%; CD29: 96.0±4.0% of the population), and were negative for hematopoietic markers (CD45:1.5±0.9%; CD34:0.7±0.6%) (FIGS. 1A-1F). ASCs exhibited multipotency evident by their ability to differentiate into osteocytes and adipocytes (FIGS. 1G-1J).

Example 2

Enhanced Migration of ASCs Following Exposure to Stressed RPE

Migration of ASCs exposed to conditioned medium of RPE under oxidative stress, was assessed. RPE were exposed to H$_2$O$_2$ as described above. As shown in FIGS. 2A-2G, the migration capacity was significantly enhanced when ASCs were exposed to conditioned medium of RPE treated with H$_2$O$_2$ (stressed RPE-CM) as opposed to exposure to conditioned medium of RPE not treated with H$_2$O$_2$ (RPE-CM) or exposure to non-conditioned medium (non-CM) (4.4±0.36-fold).

Under the same conditions, the expression of SDF-1 in stressed RPE cells was increased significantly when compared to the expression of SDF-1 in RPE without H$_2$O$_2$ treatment (2.4±0.086-fold; FIG. 2H). Accordingly, exposure of ASCs to the conditioned medium of stressed RPE resulted in increased expression of the SDF-1 receptor, CXCR4 (12.6±4.5-fold; FIG. 2I).

Example 3

ASCs Rescue RPE From Necrosis Under Oxidative Stress In Vitro

Next, the inventors assessed the protective role of ASCs' conditioned medium on RPE cells exposed to H$_2$O$_2$. RPE cells were pre-incubated for 48 h with either ASCs' conditioned medium at passage 3 (P3-CM), ASCs' conditioned medium at passage 5 (P5-CM) or non-conditioned ADSC serum free medium (non-CM), followed by H$_2$O$_2$ (1 mM, 7 h) treatment. RPE cells exposed to P3-CM prior to H$_2$O$_2$ treatment exhibited a decrease in cell death evident by FACS analysis for propidium iodide (50.6±1.6% cell death reduction) while P5-CM as well as non-CM had no effect on cell viability (FIG. 3A-3E). Furthermore, stressed RPE rescued by P3-CM were also detected by Ethidium bromide and Acridine orange staining assay (51.5% cell death reduction from total cell death counted in RPE cells exposed to H$_2$O$_2$ only; FIGS. 3F-3G).

Example 4

ASCs Overexpress Neurotropic Protein but not an Angiogenesis Factor and a Pro-Inflammatory Cytokine Examination of the expression levels of several cytokines and growth factors secreted by ASCs revealed that ASCs consistently expressed high levels of hepatocyte growth factor (HGF), lower levels of vascular endothelial growth factor (VEGF), and unchanged expression levels of IL-1β (FIG. 4A; HGF: 2.55±0.26-fold, VEGF: 1.18±0.1-fold, IL-1β: 0.31±0.14-fold). Results were compared to a control group of ASCs at passage 5 in senescence, evident by high passage, low proliferation and poor morphology. The expression of HGF was further validated at the protein level by ELISA and was demonstrated to increase by 2.9-folds of the control (FIG. 4B).

Further, a comprehensive examination comparing the cytokine secretion profile of ORBASC to ABASC, was performed. The inventors used the RayBio® Human Cytokine Antibody Array 10. Medium containing secreted proteins of ASCs which was collected from 4 different donors from each cell type, was assayed. The most abundant proteins in all samples were Angiogenin, TIMP-1, TIMP-2 and Osteoprotegerin. Nineteen (19) proteins were expressed at higher levels (above 1.5-fold increase) in ASCs from orbital origin (i.e., ORBASC) compared to abdominal origin, and 11 proteins were expressed at lower levels (above 1.5-fold decrease) in ASCs from orbital origin (i.e., ORBASC) compared to abdominal origin (Table 1).

TABLE 1

| Cytokine secretion profile | | |
|---|---|---|
| Protein | Or/Ab | T-test |
| HGF | 7.22 | 0.232026 |
| IGFBP-1 | 3.24 | 0.215429 |
| GCP-2 | 2.81 | 0.19767 |
| MIP-3b | 2.48 | 0.107946 |
| uPAR | 2.34 | 0.468506 |
| GRO | 2.11 | 0.364657 |
| IGFBP-2 | 2.09 | 0.148215 |
| IGFBP-6 | 2.09 | 0.080915 |
| ENA-78 | 2.02 | 0.447661 |
| Angiopoietin-2 | 1.82 | 0.365956 |

TABLE 1-continued

Cytokine secretion profile

| Protein | Or/Ab | T-test |
|---|---|---|
| SCF | 1.75 | 0.211053 |
| VEGF-D | 1.71 | 0.174917 |
| IGFBP-4 | 1.69 | 0.539368 |
| MSP-a | 1.66 | 0.351102 |
| TRAIL R4 | 1.64 | 0.284153 |
| IL-6 R | 1.64 | 0.15279 |
| IL-12 p40 | 1.62 | 0.214734 |
| NT-4 | 1.57 | 0.410651 |
| NAP-2 | 1.56 | 0.556377 |
| CK beta 8-1 | −1.55 | 0.530798 |
| ICAM-1 | −1.80 | 0.279184 |
| Leptin | −1.84 | 0.396733 |
| MCP-2 | −1.90 | 0.319929 |
| Axl | −2.00 | 0.360085 |
| EGF | −2.03 | 0.288589 |
| Osteoprotegerin | −2.66 | 0.078889 |
| I-309 | −2.75 | 0.18135 |
| MIF | −3.82 | 0.246924 |
| MCP-3 | −5.73 | 0.30244 |
| RANTES | −6.42 | 0.242958 |

Example 5

Sub-Retinal Injection of ASCs Rescues RPE Degeneration

Figure 6A:
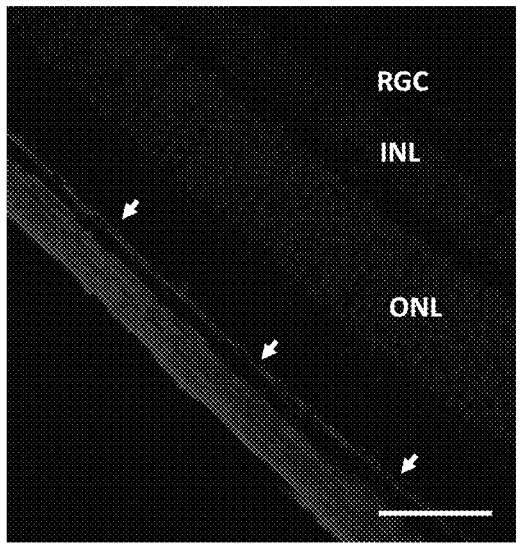
FIGS. 6A-6C are fluorescent images of the retinal pigment layer (RPE). Retinal slices were stained for the retinal pigment epithelium-specific 65 kDa protein (RPE65 antibody; red) and cell nuclei (DAPI; blue). No treatment (6A); $NaIO_3$ treatment (6B); and $NaIO_3$ treatment and ASCs treatment (6C). RPE layer staining was stronger in the eyes that received treatment with ASCs (6C). Arrows (yellow) point to the RPE layer. Bar=50 μm, ONL—outer nuclear layer, INL—inner nuclear layer, RGC—retinal ganglion layer.
Figure 6B:
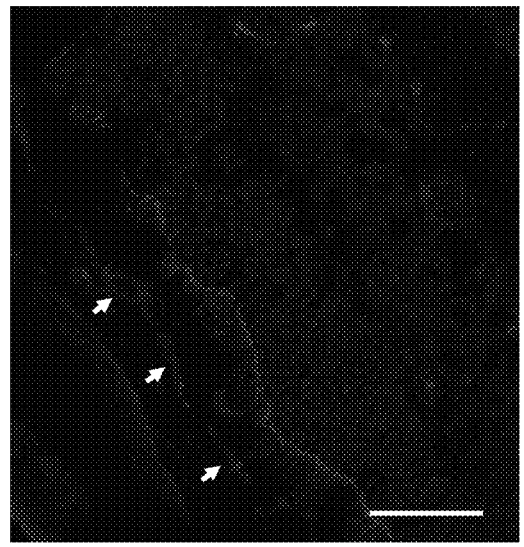
Figure 6C:
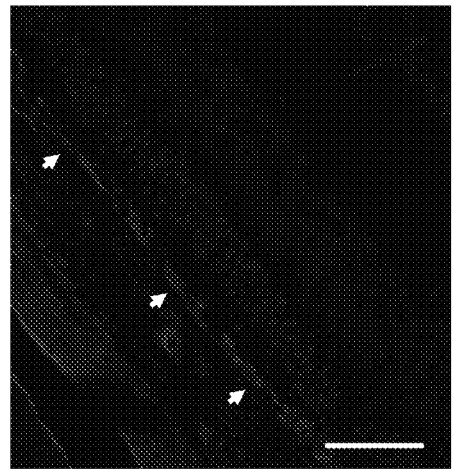
Figure 7A:
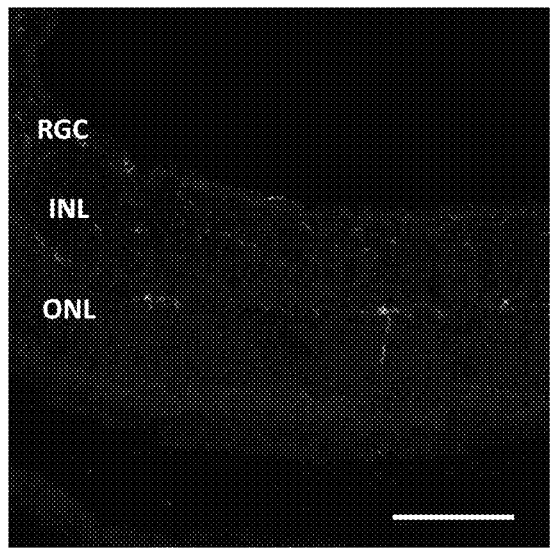
FIG. 7A-7D comprises fluorescent images demonstrating microglia activation and migration into the retina. Retinal slices were stained for the microglia-specific Ionized calcium binding adaptor molecule 1 (Iba1 antibody; green) and cell nuclei (DAPI; blue). No treatment (7A); $NaIO_3$ treatment (7B); $NaIO_3$ treatment and PBS (7C); and $NaIO_3$ treatment and ASCs treatment (7D). Microglial activation was seen in all the eyes that were exposed to $NaIO_3$. However, the largest amounts of microglia activation and migration into the retina (arrow heads) were observed in the experiment group that was treated with ASCs (7D). Bar=100 μm, ONL—outer nuclear layer, INL—inner nuclear layer, RGC—retinal ganglion layer.
Figure 7B:
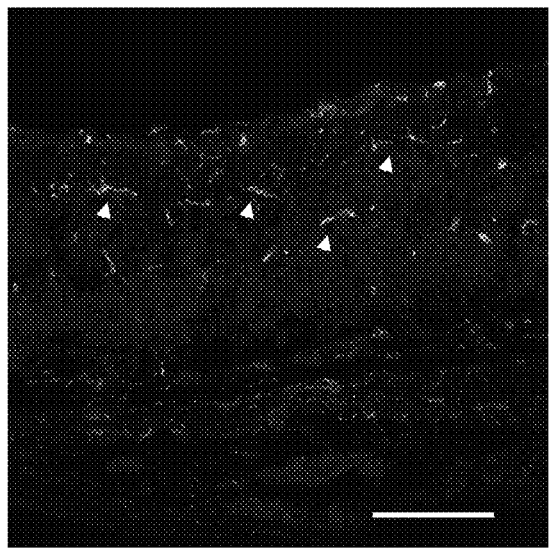
Figure 7C:
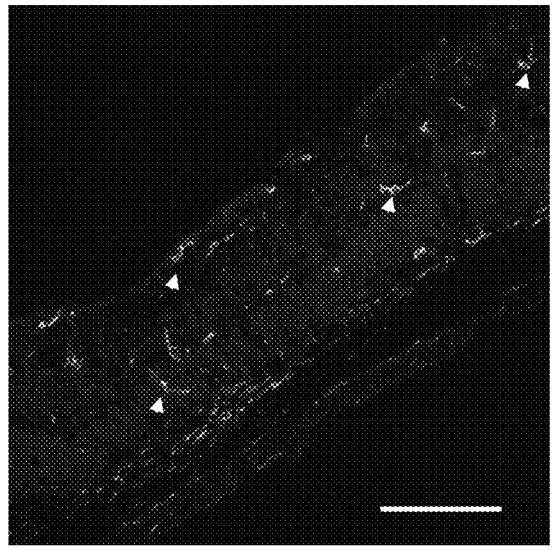
Figure 7D:
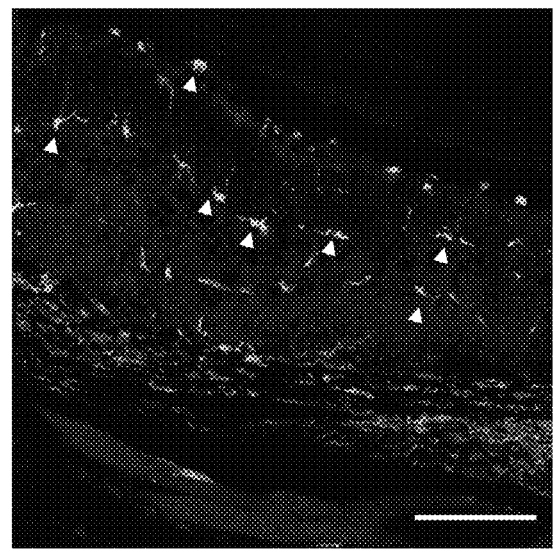
Figure 8A:
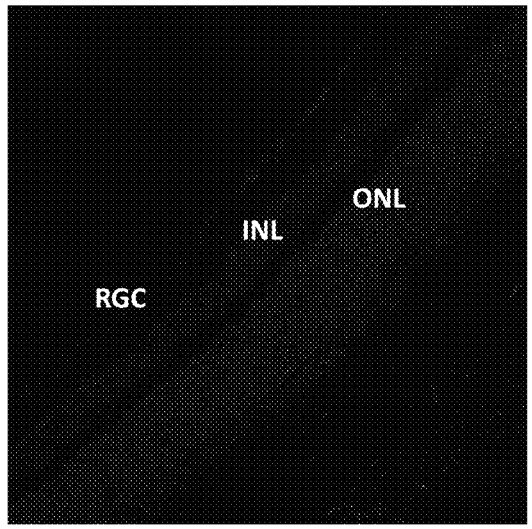
FIG. 8A-8D are fluorescent images demonstrating cell proliferation. Retinal slices were stained for antigen Ki67 proliferation marker (Ki67 antibody; green) and cell nuclei (DAPI; blue). No treatment (8A); $NaIO_3$ treatment (8B); $NaIO_3$ treatment and PBS (8C); and $NaIO_3$ treatment and ASCs treatment (8D). Proliferating cells (arrow heads) were observed mainly in the choroid of eyes treated with ASCs (8D) Bar=100 μm, ONL—outer nuclear layer, INL—inner nuclear layer, RGC—retinal ganglion layer.
Figure 8B:
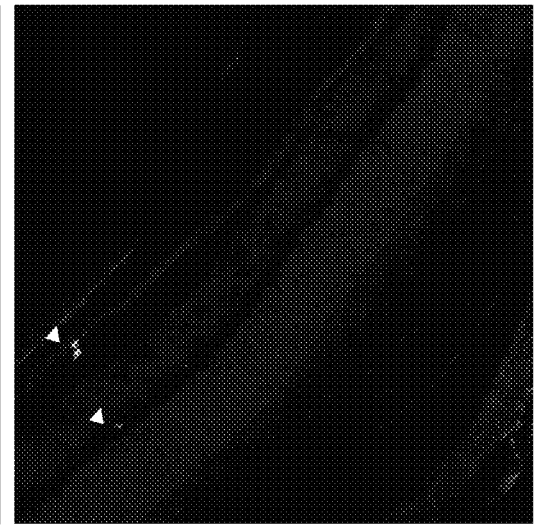
Figure 8C:
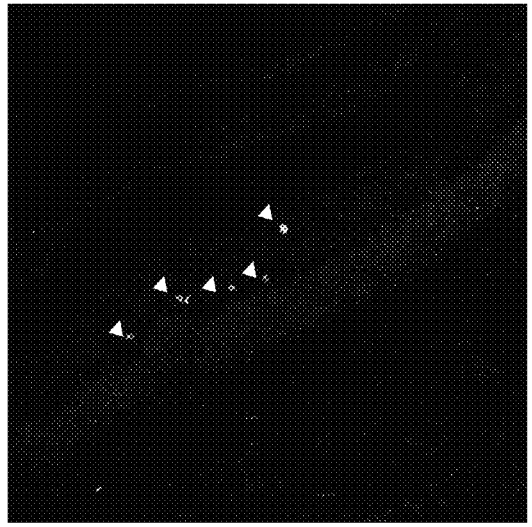
Figure 8D:
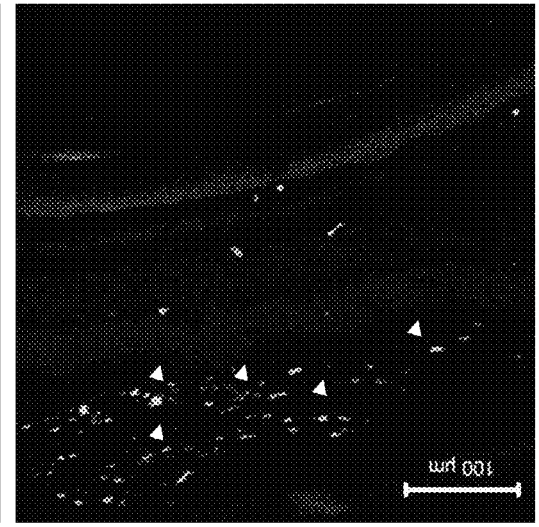
Figure 9A:
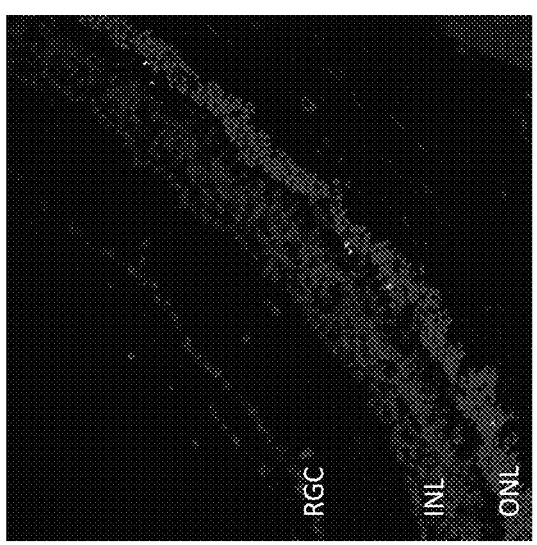
FIGS. 9A-9F are fluorescent images demonstrating cell death. Retinal slices were stained for cell nuclei (9A-9C; DAPI) and apoptotic cells (9D-9F; TUNEL kit) and. $NaIO_3$ treatment and ASCs treatment (9A and 9D); $NaIO_3$ treatment and PBS (9B and 9E) and No treatment (9C and 9F). Apoptotic cells were observed mainly in the outer nuclear layer (ONL). No difference was detected between the control and experiment groups. Arrows (yellow) indicate apoptotic cells. Bar=100 µm, ONL—outer nuclear layer, INL—inner nuclear layer, RGC—retinal ganglion layer.
Figure 9B:
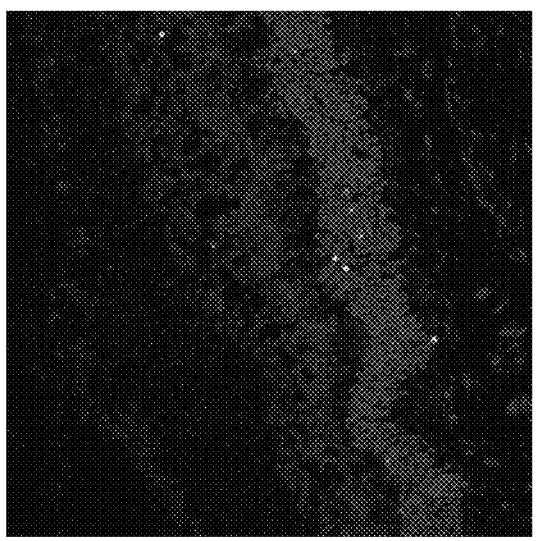
Figure 9C:
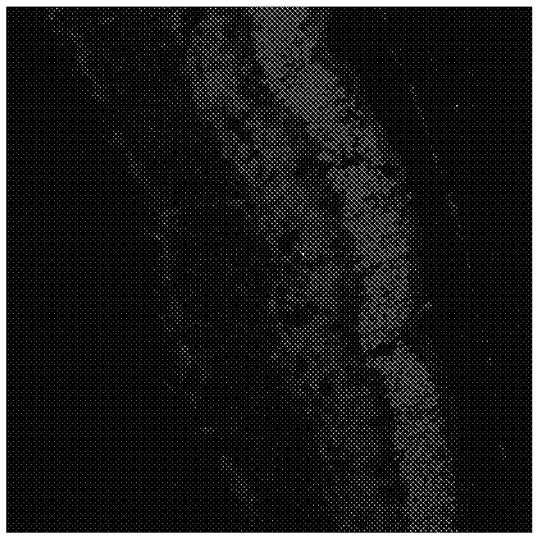
Figure 9D:
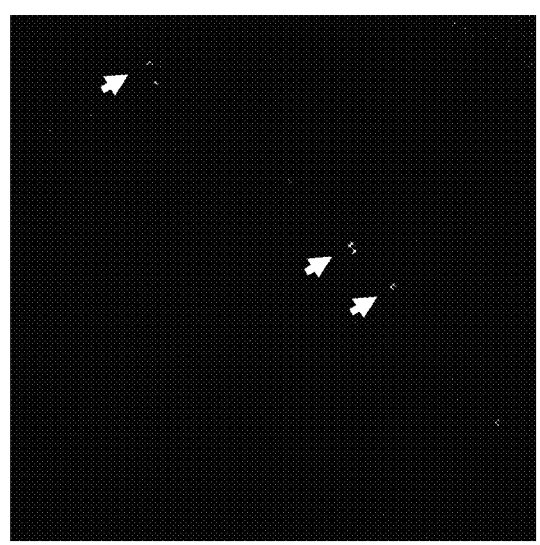
Figure 9E:
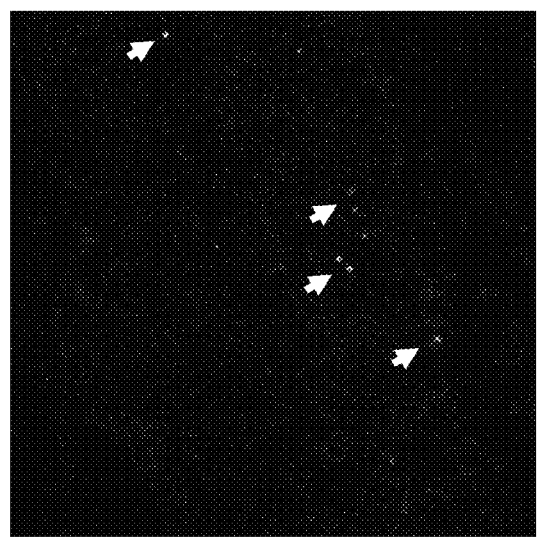
Figure 9F:
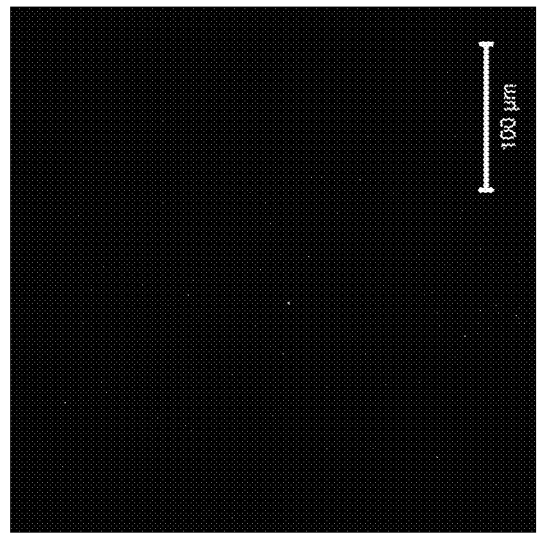
Figure 10C:
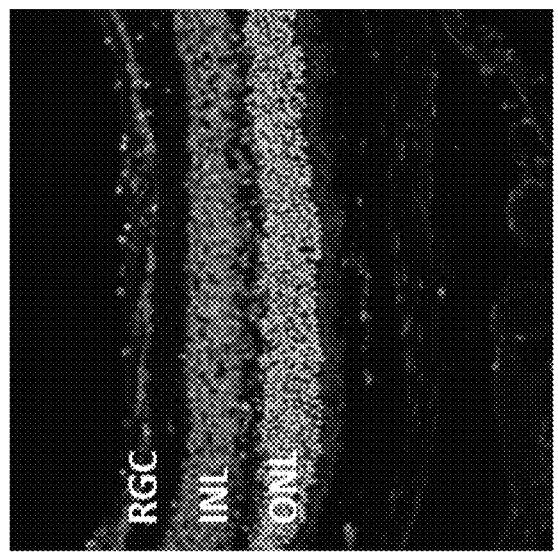
FIGS. 10A-10D are images and a graph demonstrating the thickness of the outer nuclear layer (ONL). Damage to the RPE layer directly affects the photoreceptor cells in the ONL. (10A-10C) are fluorescent images of retinal slices from: No treatment (10A); NaIO$_3$ treatment and PBS (10B); and NaIO$_3$ treatment and ASCs treatment (10C), which were stained for cell nuclei (sytox blue). (10D) is a vertical bar graph showing the thickness of the ONL, which was measured by ImageJ software. Ten (10) days after NaIO$_3$ injection the ONL of retinas treated with ASCs (10C) was thicker than ONL of PBS treated retinas (NaIO$_{3+}$PBS; p<0.05). ONL—outer nuclear layer, INL—inner nuclear layer, RGC—retinal ganglion layer.
Figure 10B:
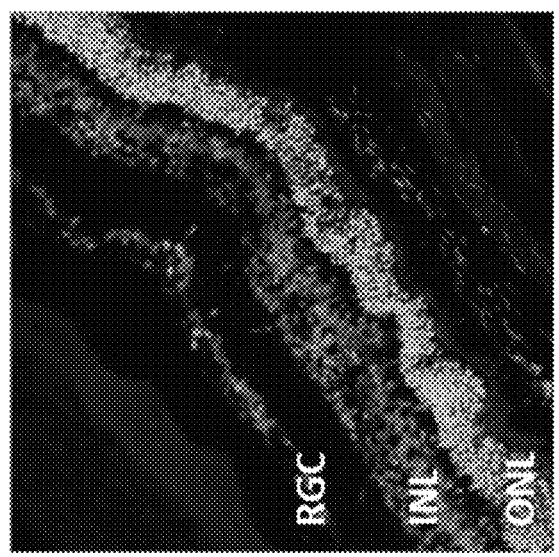
Figure 10A:
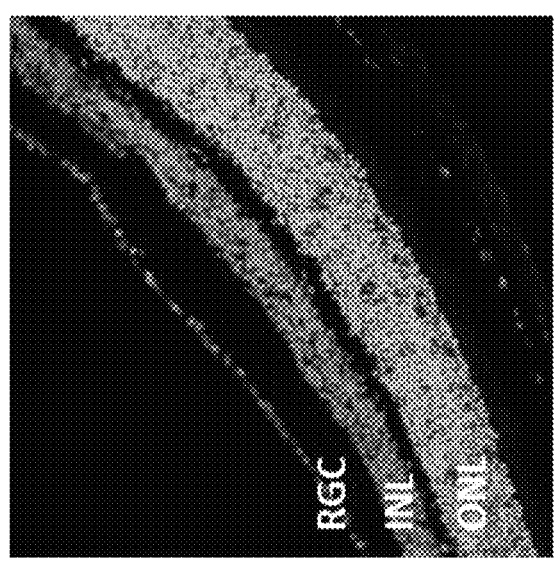
Figure 10D:
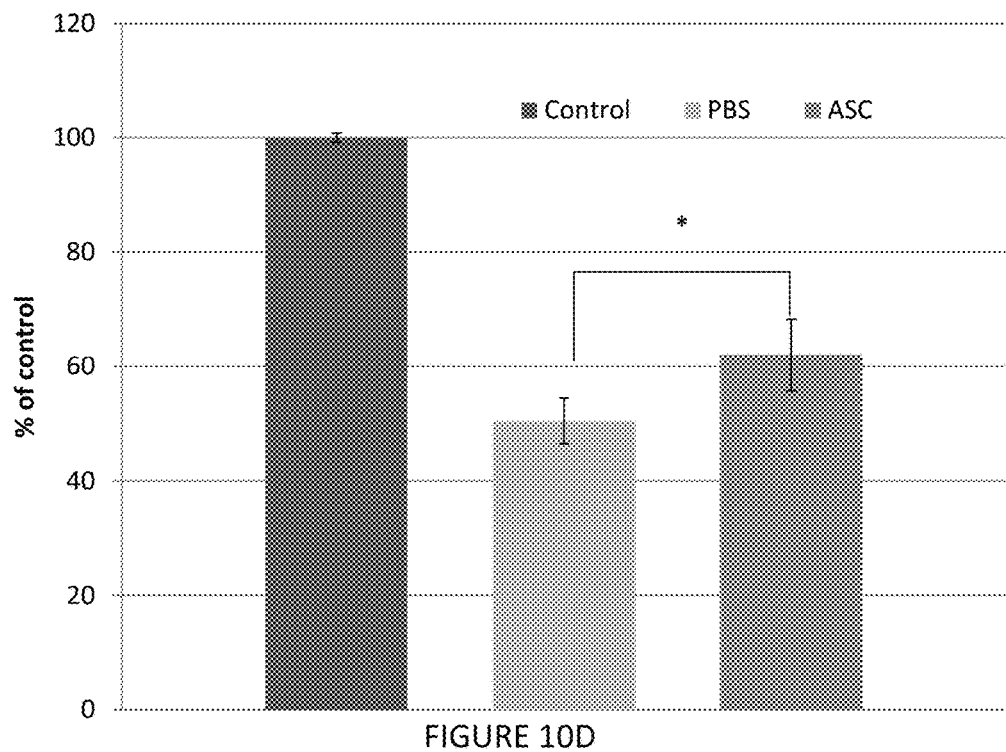
Figures 11A, 11B, 11C:
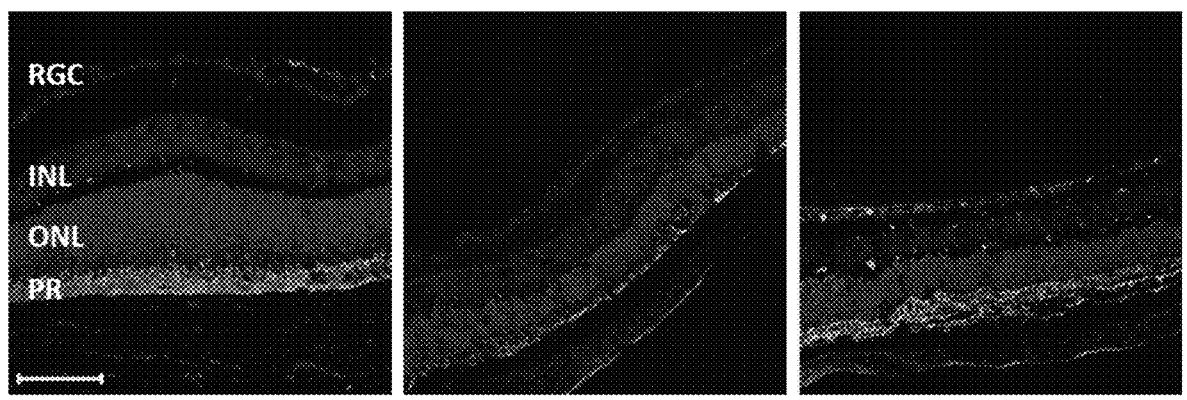
FIGS. 11A-11E are images and graphs demonstrating the size of the photoreceptor layer and rhodopsin labeling intensity. NaIO$_3$ injection damages the RPE layer that nourishes the photoreceptor layer. Rhodopsin is a light sensitive protein found in rod cells. (11A-11C) are fluorescent images of retinal slices from: No treatment (11A); NaIO$_3$ treatment and PBS (11B); and NaIO$_3$ treatment and ASCs treatment (11C), which were stained for cell nuclei (propidium iodide) and rhodopsin (rhodopsin antibody). (11D) is a vertical bar graph describing the size of the photoreceptor layer. (11E) is a vertical bar graph showing the intensity of the rhodopsin signal. (11D-11E) were measured by ImageJ software. The photoreceptor layer in retinas treated with ASCs was larger and rhodopsin labeling intensity higher than in PBS treated retinas (NaIO$_3$+PBS) (*p<0.05, **p<<0.05). PR—photoreceptor layer, ONL—outer nuclear layer, INL—inner nuclear layer, RGC—retinal ganglion layer.
Figures 11D, 11E:
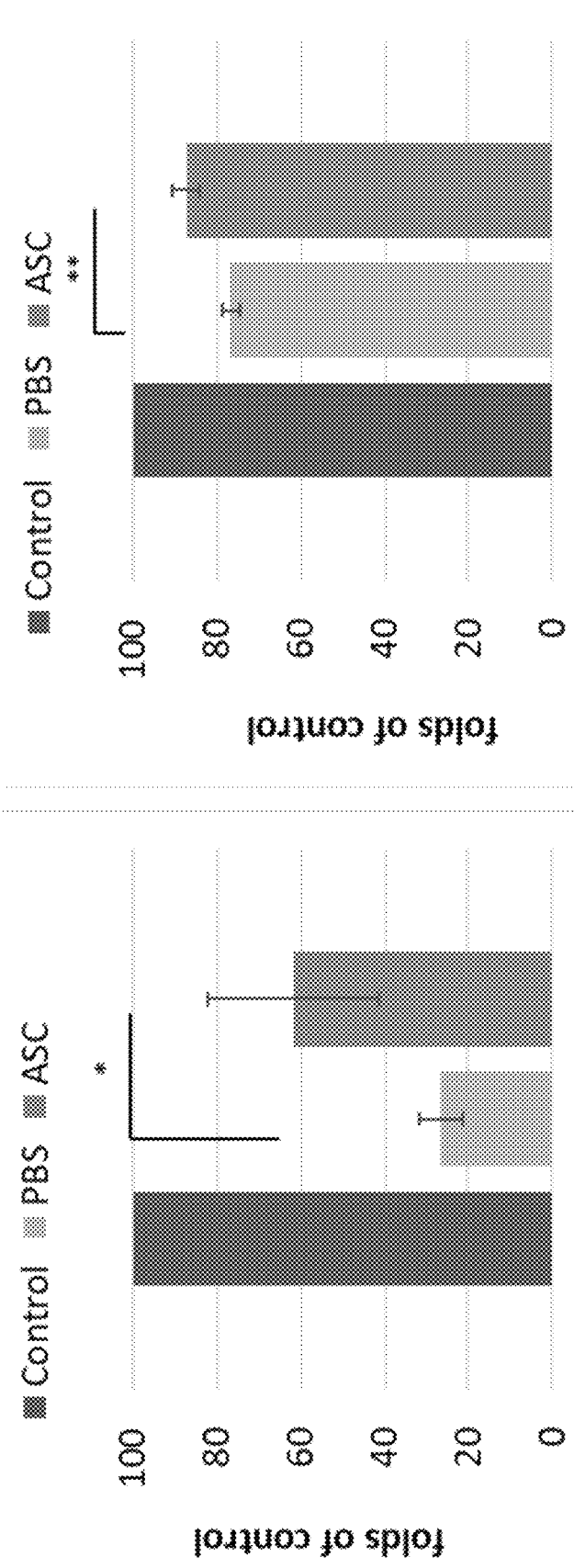

Next, the inventors assessed the protective role of ASCs on RPE tissue exposed to NaIO$_3$, in vivo. Upon injection of NaIO$_3$, Müller cells were found to be activated in the retina of mice from groups of the experiment (FIG. 5). Nonetheless, the inventors found that this effect was more pronounced in eyes that received sub-retinal injection. In contrast to the control group (sub-retinal injection of PBS), RPE layer of eyes that received treatment with ASCs, was stained stronger (FIG. 6) and comparably as eyes of the negative control group (no NaIO$_3$). While microglial activation was seen in all the eyes that were exposed to NaIO$_3$, the inventors found that the largest amounts of microglia activation and migration into the retina were observed in the experiment group that was treated with ASCs (FIG. 7), which was also accompanied by substantial cell proliferation observed mainly in the choroid (FIG. 8). Using a TUNEL assay, the inventors examined the extent of cell apoptosis in the different layers of the retina, which turned out to be indistinguishable between the different experimental groups (FIG. 9). The NaIO$_3$ administration which damaged the RPE layer directly affected the photoreceptor cells in the outer nuclear layer (ONL; FIGS. 10A-10C). Ten (10) days after the NaIO$_3$ injection, the ONL of retinas treated with ASCs was significantly thicker than ONL of PBS treated retinas (FIGS. 10B-10D). The latter observation was further examined based on the size of the photoreceptor layer and labeling intensity of the light sensitive protein, rhodopsin (FIG. 11). The inventors observed that the photoreceptor layer in retinas treated with ASCs was both significantly larger and rhodopsin labeling intensity higher than in PBS treated retinas (FIGS. 11D-11E). These results achieved by ASC sub-retinal injection were comparable (non-statistically different) from negative control (no NaIO$_3$).

Example 6

Evaluation of OMSC Differentiation to RPE Using a Co-Culture System

Figures 12A, 12B, 12C:
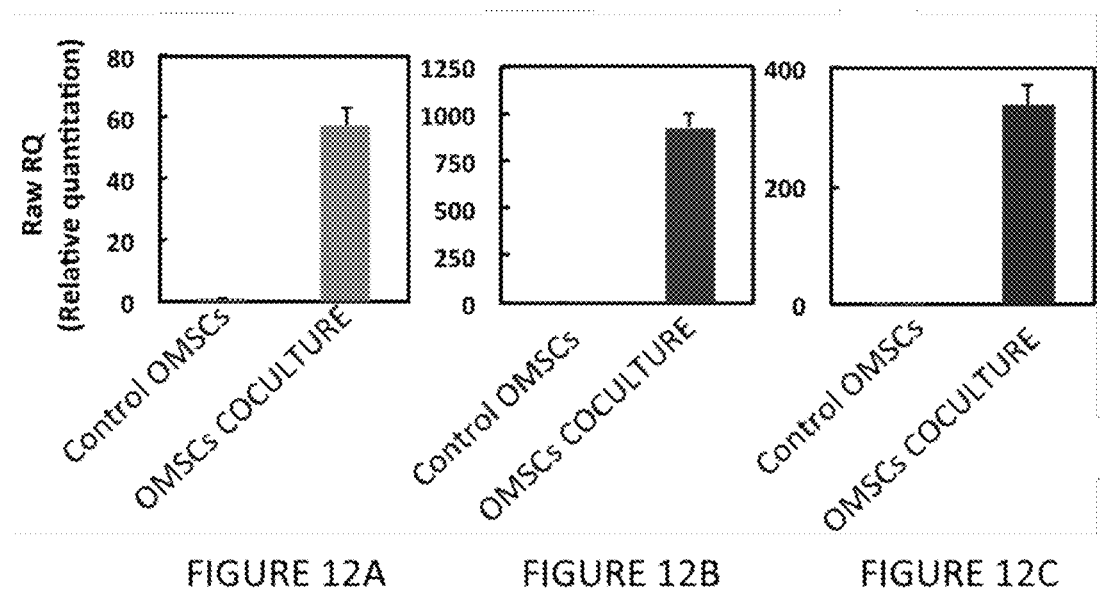
FIGS. 12A-12C are vertical bar graphs showing Orbital mesenchymal stem cells (OMSCs) overexpress eyefield markers. OMSCs at passage 3 were co-cultured with $1\times10^6$ ultra violet stained primary human RPE cells for one week after which cells were collected and analyzed at the mRNA by qRT-PCR. (12A) paired box protein-6 (PAX6). (12B) orthodenticle homeobox 2 (OTX2). (12C) SIX homeobox 3 (SIX3). Raw RQ values were compared for OMSC monoculture per each tested gene and are presented as mean±s.d. PAX6: 57.6±5.6; OTX2: 929.7±76.2; and SIX3: 338.2±33.0.

Next, the inventors examined the differentiation capacity of isolated OMSC. The direction of differentiation became clear when examining the fold increase in translation of Otx2, an early neural marker. Gene expression of Otx2 was up-regulated (929.7±76.2; FIG. 12B) and had the highest fold increase in comparison to other gene tested. The expression of Pax6, an ectodermal marker and early eye field marker, and Six3, an early eye field marker, (Pax6-57.6±5.6, Six3-338.2±33.0) was also higher for co-cultured OMSC in comparison to the control but to a smaller extent (FIGS. 12A and 12C).

Example 7

OMSC Protective Effect on Oxidatively-Stressed RPE Cells In Vitro

Figures 13A, 13B, 13C:
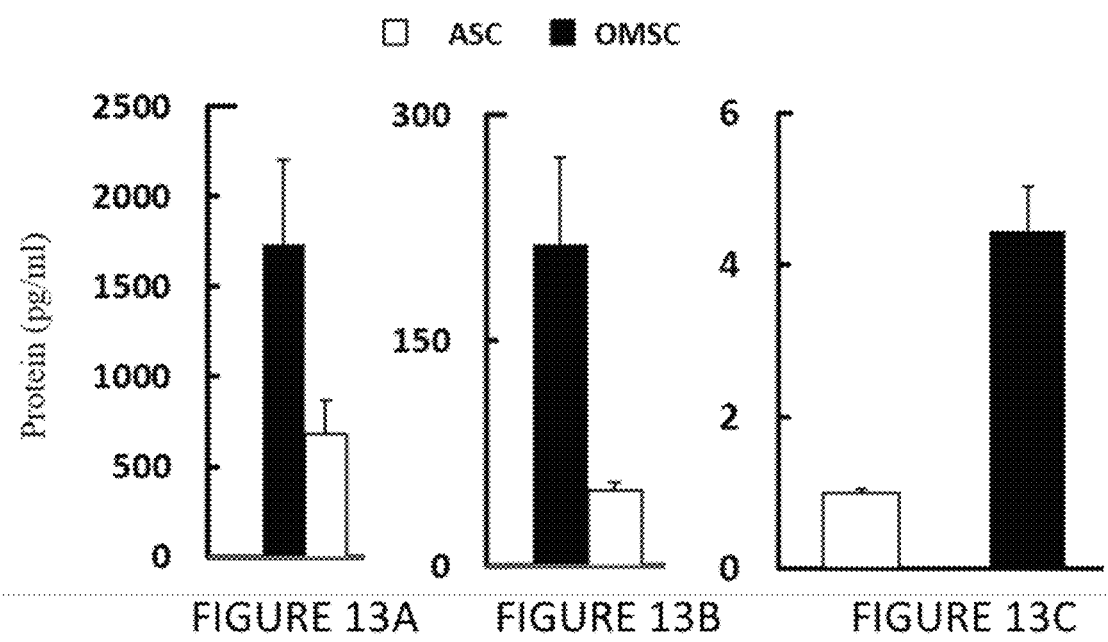
FIGS. 13A-13C are vertical bar graphs of ELISA analysis for secretion levels of (13A) insulin-like growth binding protein 6 (IGFBP-6), (13B) macrophage inflammatory protein-3-beta (MIP-3-beta), and (13C) hepatocyte growth factor (HGF) protein levels (pg/ml) in a culture. Orbital-derived mesenchymal cells (OMSC) were found to secrete significantly more levels (of each protein) compared to abdominal-derived mesenchymal cells (ASC).
Figure 14A:
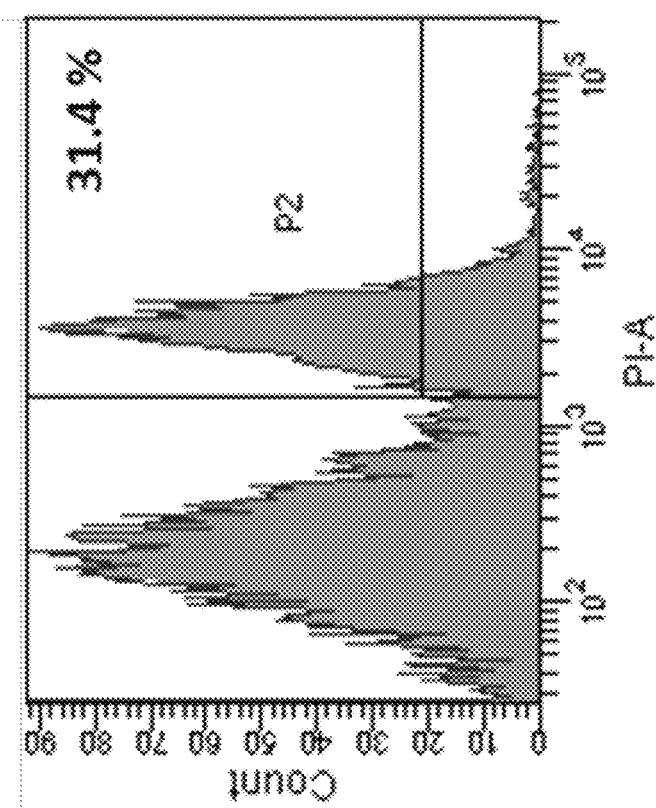
FIGS. 14A-14D are graphs demonstrating that OMSCs rescue RPE from necrosis under oxidative stress. RPE cells were incubated with OMSCs' conditioned medium (14A), or with control comprising non-conditioned ADSC medium (14B) for 48 hours, followed by exposure to $H_2O_2$ (1 mM, 7 h), cells were harvested, and cell-death was analyzed. Control non-stressed RPE cells were also used (14C). Cells were harvested, cell-death was analyzed using PI staining followed by flow cytometer analysis, and results were summarized in vertical bar graph (14D). CM: condition medium, PI: Propidium iodide.
Figure 14B:
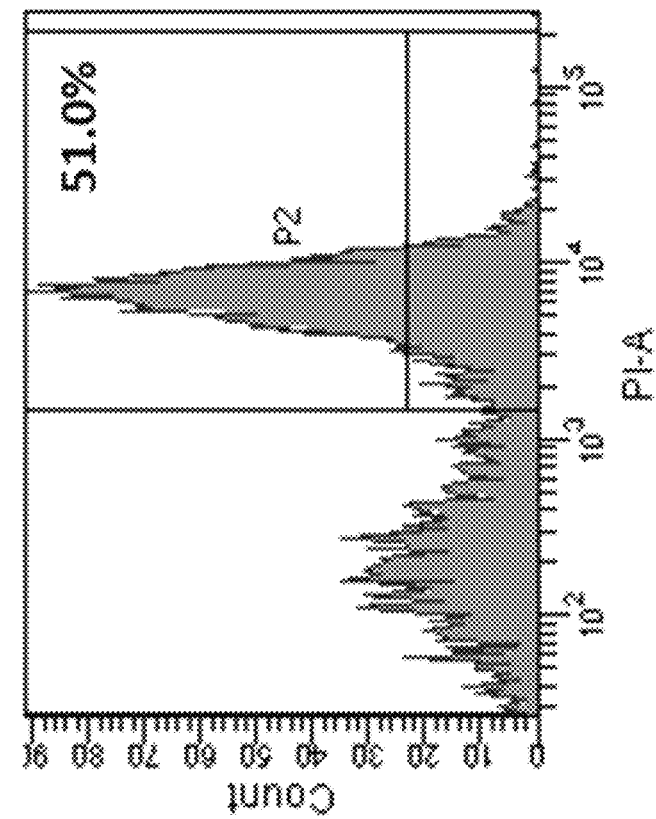
Figure 14D:
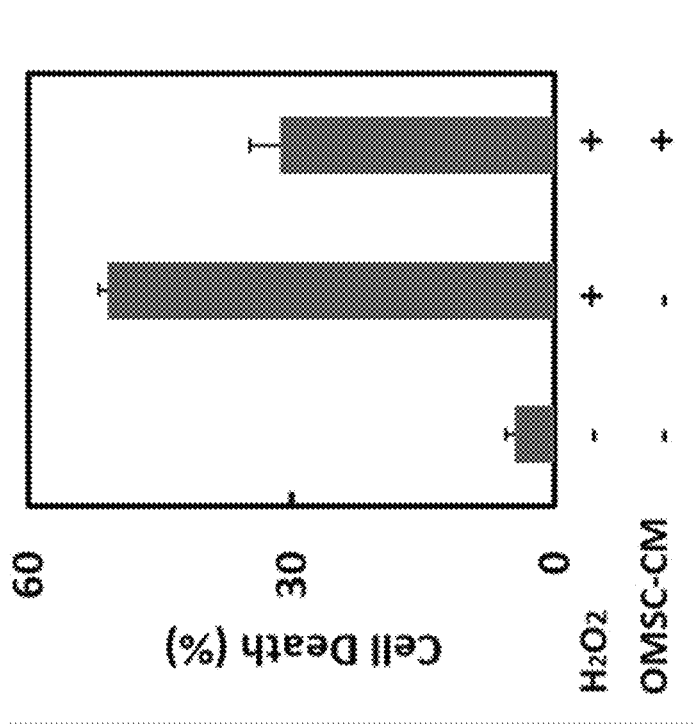
Figure 14C:
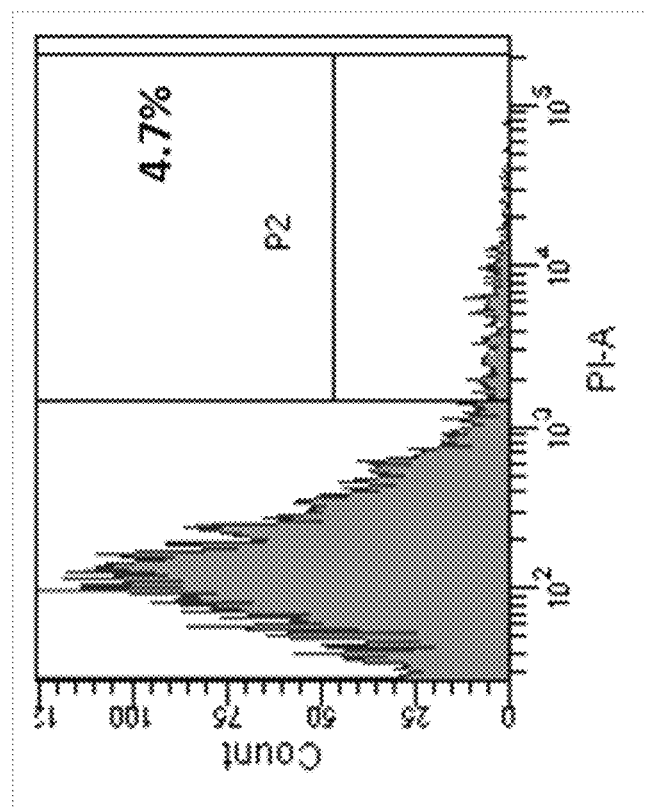

Next, the inventors examined the protective effect of isolated OMSC. The latter were found to reduce oxidatively-stressed RPE cells' necrosis by ~40% (data not shown). The expression profile of OMSC was shown to secrete significantly increased amounts of IGFBP-6 (1,737±463.8; FIG. 13A), and MIP-3beta and HGF in culture (FIGS. 13B-13C).

Example 8

OMSCs Rescue RPE from Necrosis Under Oxidative Stress In Vitro

Next, the inventors assessed the protective role of OMSCs conditioned medium on RPE cells exposed to H$_2$O$_2$. RPE cells were pre-incubated for 48 h with either OMSCs conditioned medium or non-conditioned ADSC serum free medium (non-OMSC CM), followed by H$_2$O$_2$ (1 mM, 7 h) treatment. RPE cells exposed to CM prior to H$_2$O$_2$ treatment exhibited a decrease in cell death evident by FACS analysis for propidium iodide while non-OMSC-CM had no effect on cell viability (FIGS. 14A-14D).

Example 9

Figure 15B:
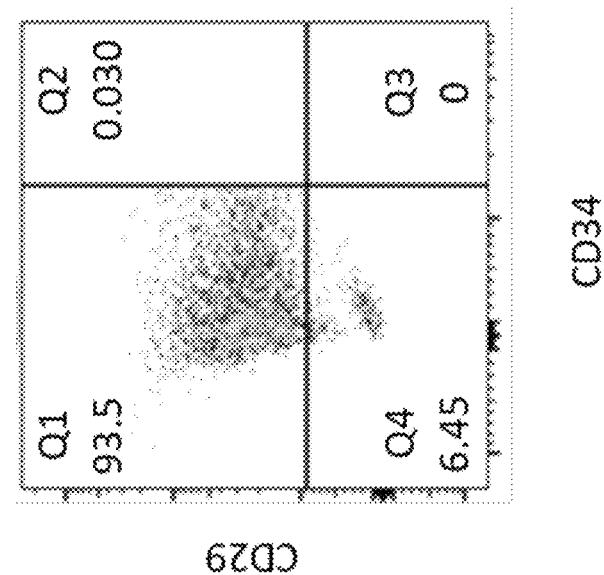
Figure 15A:
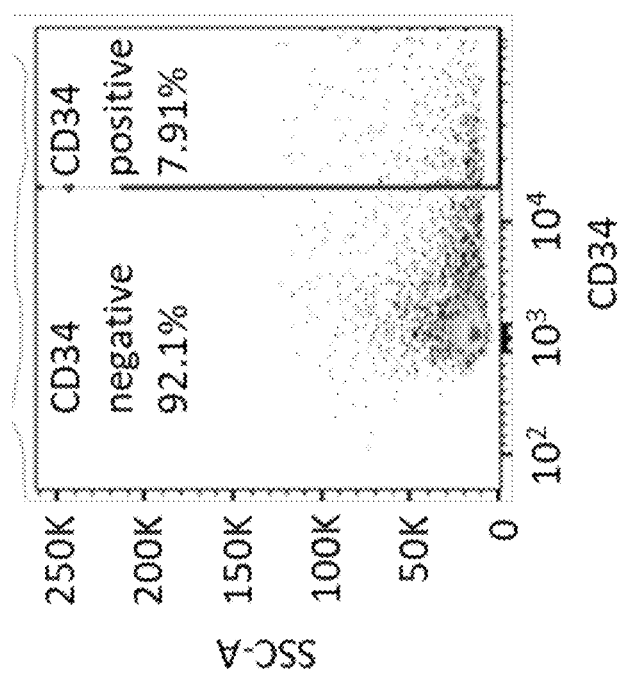

Populations of CD34-Positive Cells are More Homogenous Compared to CD34-Negative Populations The aforementioned antibody panel (comprising 6 markers) allowed a more detailed examination of potential sub-populations within the sample. ORBASCs were found to contain relatively high percentage of CD34 positive cells (8.7% on average, FIG. 15A) compared to abdominal ASCs, which had little to no CD34 positive cells. Interestingly, while CD34 negative ORBASCs displayed a relatively heterogeneous distribution of the remaining 5 markers, CD34 positive cells were much more homogenous. In a preliminary analysis, the inventors found that CD29 had a variable expression level within the CD34 negative population (10.2±7.6% of the cells were negative to CD29; FIGS. 15B and 15D) compared to CD34 positive population, where CD29 was negative in only 0.8±0.7% of the cells (FIGS. 15C-15D).

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A composition comprising orbital fat derived mesenchymal cells (OASC) and a carrier, wherein at least 70% of said OASCs within said composition express CD73, at least 70% of said OASCs lack expression of CD45, 30 to 60% of said OASCs express CD90, and 40 to 70% of said OASCs express CD105, and wherein said OASCs are characterized by 2-fold to 3-fold increased expression of a neurotrophic cytokine being hepatocyte growth factor (HGF) compared to abdominal fat derived mesenchymal cells.

2. The composition of claim 1, wherein at least 70% of said mesenchymal cells further express CXCR4, paired box protein-6 (PAX6), orthodenticle homeobox 2 (OTX2), SIX homeobox 3 (SIX3) or any combination thereof.

3. The composition of claim 1, wherein 1 to 30% of said mesenchymal cells express CD34.

4. The composition of claim 1, wherein at least 70% of said OASCs express CD90, and at least 70% of said OASCs express CD105.

5. The composition of claim 1, wherein at least 50% of said mesenchymal cells express an anti-inflammatory cytokine.

6. The composition of claim 1, wherein at least 50% of said mesenchymal cells express said neurotrophic cytokine.

7. The composition of claim 1, wherein at least 50% of said mesenchymal cells are migratory cells.

8. The composition of claim 1, further comprising a scaffold carrying said mesenchymal cells.

9. A method for treating or preventing retinal pigment epithelium (RPE) cells degeneration in a subject in need thereof, comprising administering to said subject the composition of claim 1.

10. A method for treating age-related macular degeneration (AMD) in a subject, comprising administering to said subject the composition of claim 1, thereby treating AMD in the subject.

11. The method of claim 10, wherein 1 to 30% of said mesenchymal cells express CD34.

12. The method of claim 9, wherein 1 to 30% of said mesenchymal cells express CD34.

13. The method of claim 9, wherein said mesenchymal cells are autologous or allogeneic cells.

14. The method of claim 10, wherein said mesenchymal cells are autologous or allogeneic cells.

15. The composition of claim 1, wherein increased expression comprises increased secretion.

16. The composition of claim 1, further being characterized by 2.5-fold to 3.5-fold increased HGF protein secretion levels compared to said control.

17. The composition of claim 1, further being characterized by 6-fold to 8-fold increased HGF protein secretion levels compared to abdominal fat derived mesenchymal stem cells control.

* * * * *

SEQUENCE LISTING

<160> NUMBER OF SEQ IDS NOS: 8

<210> SEQ ID NO 1
<211> LENGTH: 26
<212> TYPE: DNA
<213> ORGANISM: Artificial Sequence
<220> FEATURE:
<223> OTHER INFORMATION: Synthetic

<400> SEQUENCE: 1
taagcctagc agtaaagaga cattgg                                          26

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
taacatctgc aagcataaac gacaa                                           25

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
acggctgcct tgccttct                                                   18

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
ctggagctct gtttggaagg a                                               21

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ccggaagagt tgtccatgtt                                                 20

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
ctcctccagc gtctcacag                                                  19

<210> SEQ ID NO 7
<211> LENGTH: 20
<212> TYPE: DNA
<213> ORGANISM: Artificial Sequence

```
<220> FEATURE:
<223> OTHER INFORMATION: Synthetic

<400> SEQUENCE: 7
accacagaag gttcatccgc                                                  20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
cagggatctg ggaaagcaca                                                  20
```